(12) United States Patent
Toki

(10) Patent No.: US 12,369,870 B2
(45) Date of Patent: Jul. 29, 2025

(54) MEDICAL IMAGE DIAGNOSIS APPARATUS AND ULTRAVIOLET-RAY IRRADIATION APPARATUS

(71) Applicant: CANON MEDICAL SYSTEMS CORPORATION, Otawara (JP)

(72) Inventor: Yusuke Toki, Kita-ku (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 1033 days.

(21) Appl. No.: 17/305,346

(22) Filed: Jul. 6, 2021

(65) Prior Publication Data

US 2022/0000439 A1    Jan. 6, 2022

(30) Foreign Application Priority Data

Jul. 6, 2020    (JP) .................... 2020-116493

(51) Int. Cl.
| | |
|---|---|
| A61B 6/00 | (2024.01) |
| A61B 6/04 | (2006.01) |
| A61L 2/10 | (2006.01) |
| A61L 2/26 | (2006.01) |

(52) U.S. Cl.
CPC .......... *A61B 6/4423* (2013.01); *A61B 6/0407* (2013.01); *A61B 6/4417* (2013.01); *A61B 6/4441* (2013.01); *A61L 2/10* (2013.01); *A61L 2/26* (2013.01); *A61L 2202/24* (2013.01)

(58) Field of Classification Search
CPC ... A61B 6/4423; A61B 6/0407; A61B 6/4417; A61B 6/4441; A61B 8/4422; A61B 6/4464; A61L 2/10; A61L 2/26; A61L 2202/24; A61L 2202/14
See application file for complete search history.

(56) References Cited

U.S. PATENT DOCUMENTS

| | | | |
|---|---|---|---|
| 12,042,572 B2 * | 7/2024 | Ooshima | A61L 2/10 |
| 2012/0008741 A1 * | 1/2012 | Hendriks | A61B 6/4423 378/63 |
| 2018/0339073 A1 * | 11/2018 | Clynne | A61L 2/0047 |
| 2021/0298703 A1 * | 9/2021 | Vestevich | A61B 6/4423 |
| 2022/0062474 A1 * | 3/2022 | Angel | A61B 6/4423 |
| 2022/0175330 A1 * | 6/2022 | Kobayashi | A61B 6/502 |
| 2022/0401047 A1 * | 12/2022 | Masahashi | A61B 6/4423 |
| 2023/0110384 A1 * | 4/2023 | Lloyd | A61Q 17/04 424/59 |
| 2023/0165992 A1 * | 6/2023 | Iwai | A61L 2/24 422/24 |

FOREIGN PATENT DOCUMENTS

| | | |
|---|---|---|
| JP | 09-253083 A | 9/1997 |
| JP | 2012-511381 A | 5/2012 |
| JP | 2013-248124 A | 12/2013 |

* cited by examiner

*Primary Examiner* — Sean E Conley
*Assistant Examiner* — Brendan A Hensel
(74) *Attorney, Agent, or Firm* — Oblon, McClelland, Maier & Neustadt, L.L.P.

(57) ABSTRACT

A medical image diagnosis apparatus according to an embodiment includes an ultraviolet light source, processing circuitry, and an imaging equipment. The ultraviolet light source emits an ultraviolet ray. The processing circuitry controls irradiation of the ultraviolet ray to an irradiation object irradiated with the ultraviolet ray in an examination room by moving a position of the ultraviolet light source relatively with respect to the irradiation object. The imaging equipment acquires a medical image of a subject.

22 Claims, 15 Drawing Sheets

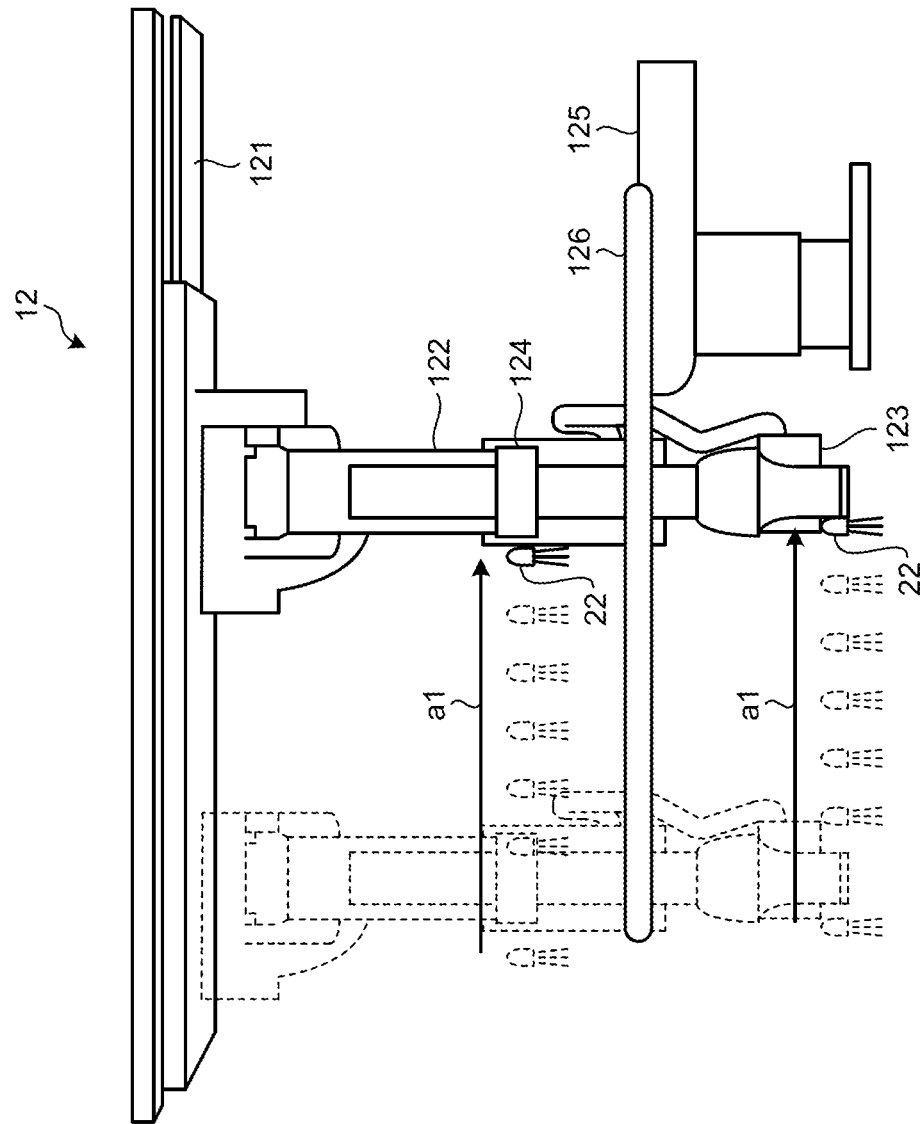

MEDICAL IMAGE DIAGNOSIS APPARATUS AND ULTRAVIOLET-RAY IRRADIATION APPARATUS

CROSS-REFERENCE TO RELATED APPLICATIONS

This application is based upon and claims the benefit of priority from Japanese Patent Application No. 2020-116493, filed on Jul. 6, 2020; the entire contents of which are incorporated herein by reference.

FIELD

Embodiments disclosed in the present specification and the drawings relate to a medical image diagnosis apparatus and an ultraviolet-ray irradiation apparatus.

BACKGROUND

Conventionally, hygiene management for preventing a nosocomial infection has been an important issue in medical facilities. For example, in the hygiene management for a medical image diagnosis apparatus, removal of attached body fluids of a subject and wiping with a disinfectant such as alcohol are common.

BRIEF DESCRIPTION OF THE DRAWINGS

FIG. 3 is a diagram illustrating one example of the medical image diagnosis apparatus according to the first embodiment;

DETAILED DESCRIPTION

According to an embodiment, a medical image diagnosis apparatus includes an ultraviolet light source, processing circuitry, and an imaging equipment. The ultraviolet light source emits an ultraviolet ray. The processing circuitry controls irradiation of the ultraviolet ray to an irradiation object irradiated with the ultraviolet ray in an examination room by moving the position of the ultraviolet light source relatively with respect to the irradiation object. The imaging equipment acquires a medical image of the subject.

Embodiments of a medical image diagnosis apparatus and an ultraviolet-ray irradiation apparatus are hereinafter described in detail with reference to the drawings. Note that the medical image diagnosis apparatus and the ultraviolet-ray irradiation apparatus according to the present application are not limited by the embodiments below. Note that the embodiment can be combined with another embodiment or a conventional technique in the range where the process content does not contradict. In the description below, similar components are denoted by a common reference symbol and overlapping descriptions are omitted.

First Embodiment

Figure 1:
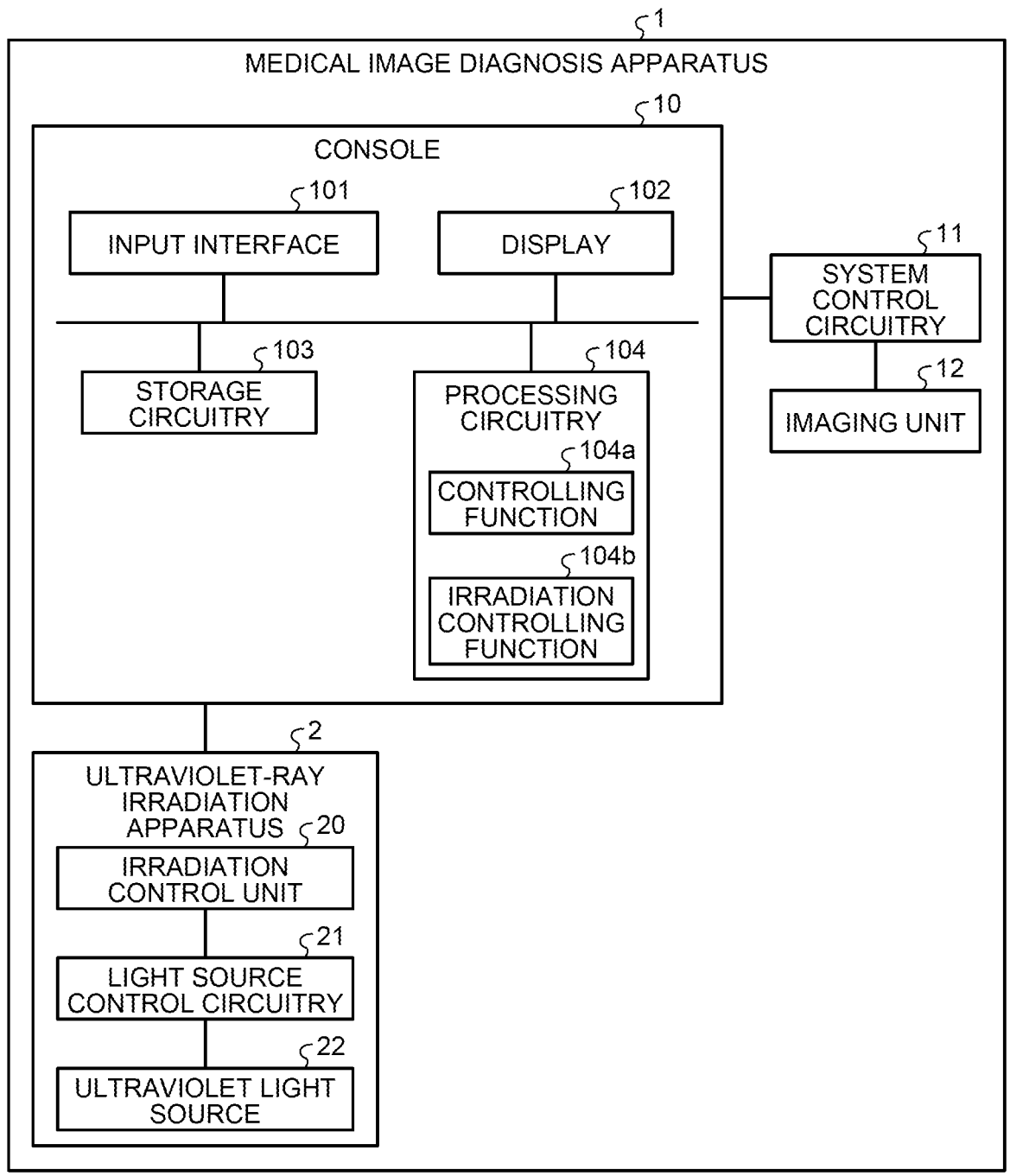
FIG. 1 is a diagram illustrating one example of a configuration of a medical image diagnosis apparatus according to a first embodiment.

FIG. 1 is a diagram illustrating one example of a configuration of a medical image diagnosis apparatus 1 according to a first embodiment. Here, with reference to FIG. 1, description is made of a case where the medical image diagnosis apparatus 1 controls the irradiation with the ultraviolet ray according to the present application.

For example, as illustrated in FIG. 1, the medical image diagnosis apparatus 1 according to the present embodiment includes a console 10, system control circuitry 11, an imaging unit 12, and an ultraviolet-ray irradiation apparatus 2. The medical image diagnosis apparatus 1 images a subject and collects medical images.

For example, the medical image diagnosis apparatus 1 is an X-ray diagnosis apparatus, an X-ray computed tomography (CT) apparatus, a magnetic resonance imaging (MRI) apparatus, an ultrasonic diagnosis apparatus, a single photon emission computed tomography (SPECT) apparatus, a positron emission computed tomography (PET) apparatus, or the like.

For example, the console 10 of the medical image diagnosis apparatus 1 includes an input interface 101, a display 102, storage circuitry 103, and processing circuitry 104 as illustrated in FIG. 1. The console 10 is connected to the imaging unit 12 through the system control circuitry 11. In addition, the console 10 is connected to the ultraviolet-ray irradiation apparatus 2.

The input interface 101 receives the input operation of various kinds of instructions and various kinds of information from a user. Specifically, the input interface 101 is connected to the processing circuitry 104, and converts the input operation received from the user into an electric signal and transmits the electric signal to the processing circuitry 104. For example, the input interface 101 is achieved by a trackball, a switch button, a mouse, a keyboard, a touch pad where input operation is performed by a touch on an operation surface, a touch screen combining a display screen and the touch pad, a non-contact input interface using an optical sensor, a voice-input interface, or the like. Note that in the present specification, the input interface 101 is not limited to only the input interface including the physical component such as a mouse or a keyboard. For example, a processing circuit for an electric signal that receives an electric signal corresponding to the input operation from an external input apparatus provided separately from the device, and outputs this electric signal to the control circuit is also included in the examples of the input interface 101.

The display 102 displays various kinds of information and various kinds of data. Specifically, the display 102 is connected to the processing circuitry 104, and displays various kinds of information and various kinds of data output from the processing circuitry 104. For example, the display 102 displays the imaged medical image, the analysis result of the medical image, or the like. The display 102 is achieved by, for example, a liquid crystal display, a cathode ray tube (CRT) display, an organic EL display, a plasma display, a touch panel, or the like.

The storage circuitry 103 stores various kinds of data and various kinds of computer programs. Specifically, the storage circuitry 103 is connected to the processing circuitry 104, and stores the data input from the processing circuitry 104, or reads out the stored data and outputs the data to the processing circuitry 104. For example, the storage circuitry 103 is achieved by a semiconductor memory element such as a random access memory (RAM) or a flash memory, a hard disk, an optical disk, or the like.

For example, the storage circuitry 103 stores a computer program to cause the circuitry included in the medical image diagnosis apparatus 1 to achieve the function. For example, the storage circuitry 103 stores a plurality of pieces of preset information for specifying the irradiation range of the ultraviolet ray, and the three-dimensional shape data of various devices and facilities disposed in an examination room where the medical image diagnosis apparatus 1 is disposed. Note that the preset information and the three-dimensional shape data are described below in detail. The storage circuitry 103 may be achieved by a server group (cloud) connected to the medical image diagnosis apparatus 1 through a network.

The processing circuitry 104 controls the entire medical image diagnosis apparatus 1. For example, the processing circuitry 104 performs a controlling function 104a and an irradiation controlling function 104b. Here, for example, the processing functions to be performed by the controlling function 104a and the irradiation controlling function 104b, which are components of the processing circuitry 104 illustrated in FIG. 1, are recorded in the storage circuitry 103 as computer-executable computer programs. The processing circuitry 104 is a processor, for example, and by reading out and executing the computer program stored in the storage circuitry 103, the processing circuitry 104 achieves the function corresponding to each computer program that is read out. In other words, the processing circuitry 104 having read out each computer program has each function illustrated in the processing circuitry 104 in FIG. 1. Note that the processing circuitry 104 is one example of the processing circuitry.

For example, the controlling function 104a performs various processes in accordance with the input operation received from the user through the input interface 101. For example, the controlling function 104a controls the imaging unit 12 by exchanging control signals, positional data, and the like with the system control circuitry 11, and collects the medical image data. In addition, the controlling function 104a generates the medical image for display on the basis of the collected medical image data, and performs various analysis processes and the like based on the medical image data. Furthermore, for example, the controlling function 104a causes the display 102 to display various kinds of information and various kinds of data.

The irradiation controlling function 104b controls the irradiation with the ultraviolet ray. The process by the irradiation controlling function 104b is described below in detail.

The system control circuitry 11 controls the imaging unit 12 on the basis of the control signal and the positional data received from the controlling function 104a. Specifically, the system control circuitry 11 controls the scan process on the subject by the imaging unit 12 on the basis of the control signal and the positional data received from the controlling function 104a, and collects the medical images.

For example, in a case where the medical image diagnosis apparatus 1 is an X-ray diagnosis apparatus equipped with a C-arm, the system control circuitry 11 drives the C-arm or a couch device and controls the irradiation with the X-ray on the basis of the control signal and the positional data received from the controlling function 104a, thereby controlling the collection of the X-ray images. In addition, for example, in a case where the medical image diagnosis apparatus 1 is an X-ray CT apparatus or an MRI apparatus, the system control circuitry 11 drives the couch device and controls the scanning by a gantry, thereby controlling the collection of CT images or MR images.

The imaging unit 12 performs a scan process for collecting the medical images of the subject. Specifically, the imaging unit 12 performs the scan process for collecting the medical images of the subject on the basis of the control signal and the positional data received from the system control circuitry 11. The imaging unit 12 is one example of an imaging equipment.

For example, in the case where the medical image diagnosis apparatus 1 is the X-ray diagnosis apparatus equipped with the C-arm, the imaging unit 12 includes the C-arm or the couch device and collects the X-ray images on the basis of the control signals or positional data received from the system control circuitry 11. In addition, for example, in the case where the medical image diagnosis apparatus 1 is the X-ray CT apparatus or the MRI apparatus, the imaging unit 12 includes the gantry or the couch device and collects the CT images or MR images on the basis of the control signals or positional data received from the system control circuitry 11.

The ultraviolet-ray irradiation apparatus 2 includes an irradiation control unit 20, light source control circuitry 21, and an ultraviolet light source 22, and is connected to the console 10 as illustrated in FIG. 1.

The irradiation control unit 20 controls the irradiation with the ultraviolet ray under the control of the processing circuitry 104. Specifically, the irradiation control unit 20 controls the irradiation of the irradiation object with the ultraviolet ray on the basis of the control signal received from the irradiation controlling function 104b. For example, the irradiation control unit 20 includes processing circuitry, a power source, and the like, and by transmitting a control signal to the light source control circuitry 21, controls the light source control circuitry 21 and causes the ultraviolet light source 22 to emit the ultraviolet ray.

The light source control circuitry 21 controls a light-emitting element in the ultraviolet light source 22 so that the ultraviolet light source 22 emits the ultraviolet ray. Specifically, the light source control circuitry 21 transmits the control signal to the ultraviolet light source 22 on the basis of the control signal received from the irradiation control unit 20 so as the control the output of the light-emitting element in the ultraviolet light source 22.

The ultraviolet light source 22 includes a light-emitting element such as a light-emitting diode (LED) or a laser diode (LD) emitting the ultraviolet ray, and emits the ultraviolet ray under the control by the light source control circuitry 21. For example, the ultraviolet light source 22 includes an LED with a peak around a wavelength of 350 nm or a deep ultraviolet-ray LED capable of emitting a deep ultraviolet-ray with a wavelength of 200 to 300 nm. Note that the ultraviolet light source 22 is one example of the ultraviolet light source.

One example of the configuration of the medical image diagnosis apparatus 1 and the ultraviolet-ray irradiation apparatus 2 according to the present embodiment has been described. With this configuration, the medical image diagnosis apparatus 1 according to the present embodiment can achieve the stable hygiene management.

As described above, in the medical facilities, the hygiene management for preventing a nosocomial infection due to drug-resistant bacteria or virus has been an important issue. For example, the hygiene management for the medical image diagnosis apparatus (and in the examination room where the medical image diagnosis apparatus is disposed) is usually performed by manually wiping the apparatus with a disinfectant such as alcohol.

However, in the case of manual wiping, the labor required for wiping before and after the examination time is significant, and the labor cost is not small, too. Additionally, in the case of manual wiping, the degree of cleanness may vary depending on the worker, and there may be cases where some places are left uncleaned. Moreover, the disinfectant may be less effective on drug-resistant bacteria or virus.

Other ways of the hygiene management than wiping may include attachment of silver nanoparticles or the like with an antimicrobial effect to a surface of a device, and use of a fixed type bactericidal lamp or a mobile sickroom sterilizer, for example. However, some medical facilities may concern that attaching the silver nanoparticles or the like to the surface of the device has an impact on human bodies and the environment. Also, when liquid from which the device is protected for bacteria has high viscosity (for example, blood) and some parts of the liquid are not in contact with the surface of the device, the effect is insufficient. The fixed type bactericidal lamp, if disposed apart from the irradiation object, requires time to sterilize the irradiation object and moreover, the shadow may interrupt the uniform sterilization. Furthermore, the mobile sickroom sterilizer, if disposed apart from the irradiation object, requires high output and the shadow may interrupt the uniform sterilization.

In view of the above, the medical image diagnosis apparatus 1 according to the present embodiment irradiates the irradiation object with the ultraviolet ray, so that the stable hygiene management can be achieved. The medical image diagnosis apparatus 1 according to the first embodiment is hereinafter described in detail.

The medical image diagnosis apparatus 1 according to the first embodiment includes the ultraviolet light source, and performs the irradiation with the ultraviolet ray while moving the position of the ultraviolet light source relatively with respect to the irradiation object irradiated with the ultraviolet ray in the examination room where the medical image diagnosis apparatus 1 is disposed. That is to say, in the medical image diagnosis apparatus 1, the ultraviolet ray is emitted while the ultraviolet light source 22 in the ultraviolet-ray irradiation apparatus 2 illustrated in FIG. 1 is moved, so that the hygiene management of the apparatus, its vicinity, and the examination room where the apparatus is disposed is performed.

Figure 2A:
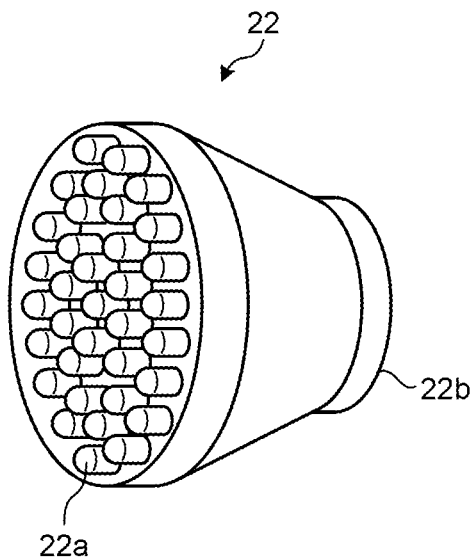
FIG. 2A is a diagram illustrating one example of an ultraviolet light source according to the first embodiment.
Figure 2B:
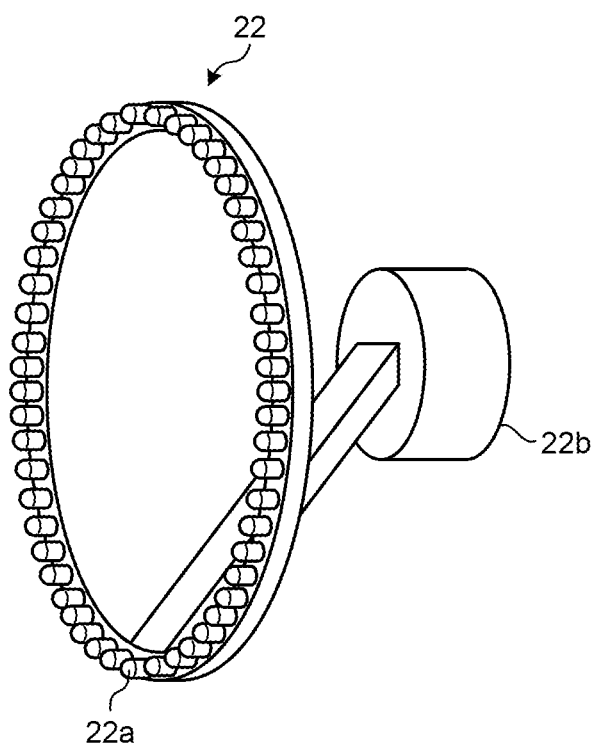
FIG. 2B is a diagram illustrating one example of the ultraviolet light source according to the first embodiment.

Here, the ultraviolet light source 22 can have a plurality of light-emitting elements such as LEDs or LDs that emit the ultraviolet ray. FIG. 2A and FIG. 2B are diagrams each illustrating one example of the ultraviolet light source 22 according to the first embodiment. As illustrated in FIG. 2A and FIG. 2B, the ultraviolet light source 22 includes a plurality of light-emitting elements 22a and an attachment part 22b. Note that the light-emitting element 22a is one example of a light generator. The attachment part 22b is an attachment part that makes a holder hold the ultraviolet light source 22.

For example, in the ultraviolet light source 22, the light-emitting elements 22a are densely arranged as illustrated in FIG. 2A. That is to say, the ultraviolet light source 22 illustrated in FIG. 2A has a configuration in which the ultraviolet rays emitted from the respective light-emitting elements 22a overlap with each other and the light quantity of the delivered ultraviolet rays concentrates.

In another example of the ultraviolet light source 22, in the light-emitting elements 22a, a gap with a predetermined size is provided between the adjacent light-emitting elements 22a. For example, in the ultraviolet light source 22, the light-emitting elements 22a are disposed in a ring shape as illustrated in FIG. 2B. That is to say, in FIG. 2B, a gap corresponding to the diameter of the ring (predetermined size) is provided between the light-emitting elements 22a facing each other (between adjacent light-emitting elements 22a) among the light-emitting elements 22a disposed in the ring shape.

Here, the size of the gap provided between the adjacent light-emitting elements 22a (the aforementioned predetermined size) is set so that the ultraviolet rays emitted from the adjacent light-emitting elements 22a overlap with each other with the minimum overlapping size. For example, between the light-emitting elements 22a facing each other among the light-emitting elements 22a disposed in the ring shape, if the radius size of the irradiation region is more than or equal to the radius of the ring, the ultraviolet rays radially emitted from the respective light-emitting elements 22a overlap with each other.

In view of this, the ultraviolet light source 22 illustrated in FIG. 2B is designed so that, for example, the radius of the ring is a little smaller than the radius size of the irradiation region of the ultraviolet ray emitted from the light-emitting element 22a. Thus, the ultraviolet ray emitted from the ultraviolet light source 22 illustrated in FIG. 2B can be delivered in the wider range and the shadow resulting from the ultraviolet ray emitted from the ultraviolet light source 22 can be minimized.

Note that FIG. 2B illustrates the example in which the gap with the predetermined size is provided between the light-emitting elements 22a corresponding to a part of the adjacent light-emitting elements 22a among the light-emitting elements 22a. However, the embodiment is not limited to this example, and the gap with the predetermined size may be provided between all the adjacent light-emitting elements 22a among the light-emitting elements 22a. In this case, for example, the light-emitting elements 22a are disposed in an array form and the gap with the predetermined size is provided between the light-emitting elements 22a in the ultraviolet light source 22. That is to say, the light-emitting elements 22a are disposed sparsely.

Note that the ultraviolet light source 22 illustrated in each of FIG. 2A and FIG. 2B is just one example, and if necessary, the light condensing degree may be increased by a combination with a lens or a concave mirror. Various other light sources may be used. For example, an ultraviolet-ray lamp, an ultraviolet-ray fluorescent lamp, or the like may be used as the ultraviolet light source 22.

The medical image diagnosis apparatus 1 according to the first embodiment includes the ultraviolet light source 22 as illustrated in FIG. 2A and FIG. 2B, for example, and while changing the relative positional relation between the ultraviolet light source 22 and the irradiation object, irradiates the irradiation object with the ultraviolet ray.

Here, in the medical image diagnosis apparatus 1 according to the first embodiment, the ultraviolet light source 22 is provided to at least one of the imaging unit and the couch where the subject is placed (lies down). The irradiation controlling function 104b operates at least one of the imaging unit and the couch where the subject is placed, thereby moving the position of the ultraviolet light source 22. That is to say, the attachment part 22b of the ultraviolet light source 22 is directly attached to the medical image diagnosis apparatus 1 according to the first embodiment, and while the movable part used to image the medical image is moved, the irradiation object is irradiated with the ultraviolet ray.

FIG. 3 to FIG. 6 are diagrams illustrating examples of the medical image diagnosis apparatus 1 according to the first embodiment. In FIG. 3, the medical image diagnosis apparatus 1 is the X-ray diagnosis apparatus equipped with a C-arm. In this case, for example, the imaging unit 12 includes a ceiling travel rail 121, a C-arm 122, an X-ray tube 123, an X-ray detector 124, and a couch device 125 including a couchtop 126.

In the X-ray diagnosis apparatus, for example, the ultraviolet light source 22 is provided to the C-arm 122. For example, as illustrated in FIG. 3, the ultraviolet light source 22 is provided to each of the X-ray tube 123 and the X-ray detector 124 held by the C-arm 122. Here, each ultraviolet light source 22 may be attached so as to deliver the ultraviolet ray to the inside and the outside of the C-arm 122.

For example, as illustrated in FIG. 3, the ultraviolet light source 22 attached to the X-ray detector 124 is set so as to deliver the ultraviolet ray to the inside of the C-arm 122. The ultraviolet light source 22 attached to the X-ray tube 123 is set so as to deliver the ultraviolet ray to the outside of the C-arm 122.

The irradiation controlling function 104b transmits the control signal and the positional data to the system control circuitry 11 so as to move the position of the ultraviolet light source 22 with respect to the irradiation object irradiated with the ultraviolet ray. Specifically, the irradiation controlling function 104b controls the irradiation of the irradiation object with the ultraviolet ray while changing the position of the ultraviolet light source 22 with respect to the irradiation object by moving the holder (C-arm) that holds the ultraviolet light source 22.

Here, the irradiation controlling function 104b determines the irradiation position of the ultraviolet light source 22 on the basis of the positional data of the holder in the coordinate system of the medical image diagnosis apparatus 1. For example, the irradiation controlling function 104b calculates the moving distance of the holder where the distance from the emission surface of the ultraviolet ray to the irradiation object becomes the distance that is set in advance, on the basis of the positional data of the holder. Then, the irradiation controlling function 104b controls the irradiation with the ultraviolet ray in a state where the holder is moved on the basis of the calculated moving distance and the distance from the emission surface of the ultraviolet ray to the irradiation object is kept.

For example, as illustrated in FIG. 3, the irradiation controlling function 104b controls the angle of the C-arm 122 so that the X-ray detector 124 is disposed on the upper side with respect to the couchtop 126 and the X-ray tube 123 is disposed on the lower side with respect to the couchtop 126. The irradiation controlling function 104b makes the C-arm 122 slide in a direction of an arrow a1 along the ceiling travel rail 121, thereby moving the position of the ultraviolet light source 22 with respect to the irradiation object irradiated with the ultraviolet ray (upper surface and floor surface of couchtop 126).

Here, the irradiation controlling function 104b transmits the control signal to the irradiation control unit 20, thereby causing the ultraviolet light source 22 to emit the ultraviolet ray. For example, the irradiation controlling function 104b transmits the control signal to the irradiation control unit 20 so that the ultraviolet ray is delivered while the C-arm 122 slides in the direction of the arrow a1. Thus, the ultraviolet ray is delivered to the upper surface and the surrounding floor surface of the couchtop 126.

Figure 4:
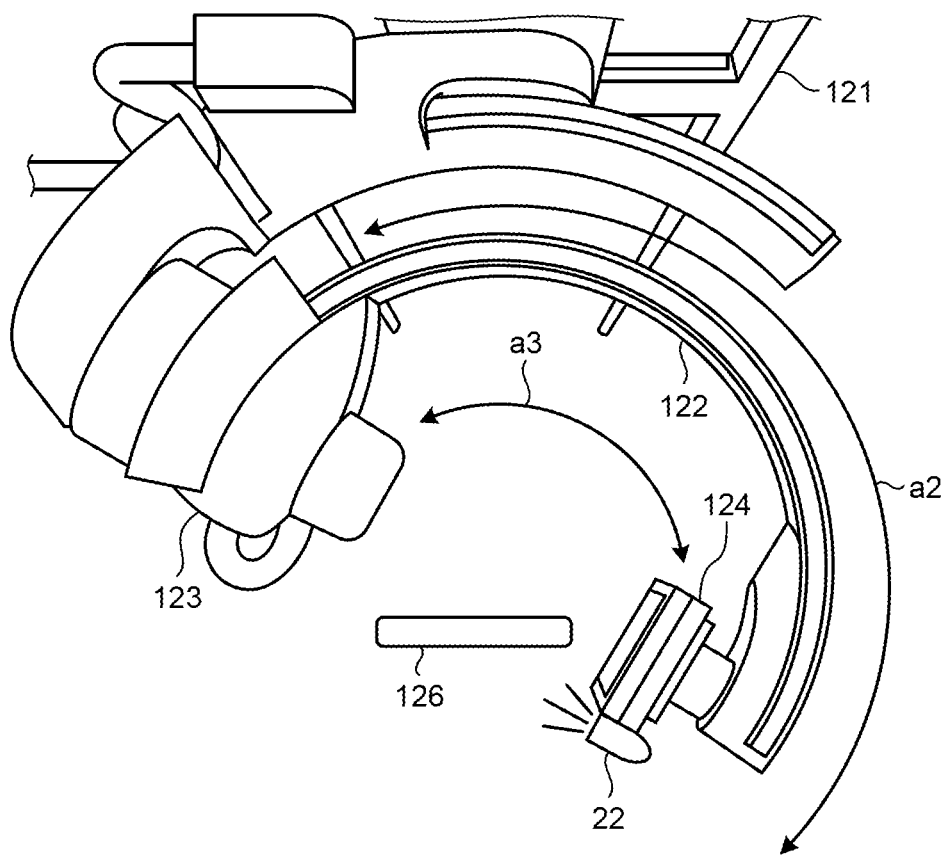
FIG. 4 is a diagram illustrating one example of the medical image diagnosis apparatus according to the first embodiment.

FIG. 4 illustrates another example of the irradiation with the ultraviolet ray in the X-ray diagnosis apparatus illustrated in FIG. 3. For example, the X-ray diagnosis apparatus can make the X-ray detector 124 and the X-ray tube 123 move along an arrow a3 by sliding the C-arm 122 along an arrow a2 as illustrated in FIG. 4.

In view of this, for example, the irradiation controlling function 104b controls the angle of the C-arm 122 so that the X-ray detector 124 is disposed on the lower side with respect to the couchtop 126 as illustrated in FIG. 4. Then, the irradiation controlling function 104b moves the position of the ultraviolet light source 22 with respect to the side surface and the lower surface of the couchtop 126 by sliding the C-arm 122 in the direction of the arrow a1 illustrated in FIG. 3 along the ceiling travel rail 121.

Then, for example, the irradiation controlling function 104b transmits the control signal to the irradiation control unit 20 so that the ultraviolet ray is delivered while the C-arm 122 slides in the direction of the arrow a1. Thus, the side surface and the lower surface of the couchtop 126 are irradiated with the ultraviolet ray.

Figure 5:
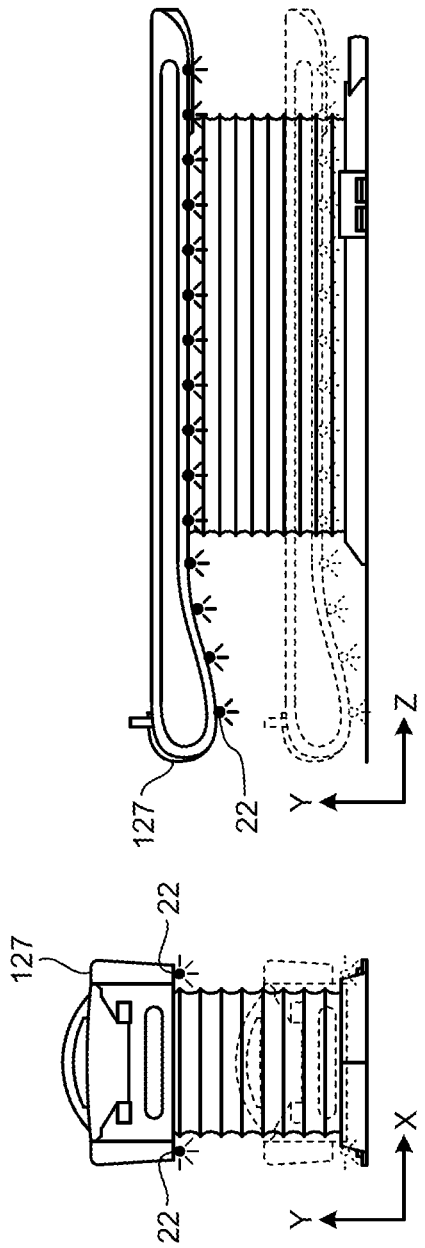
FIG. 5 is a diagram illustrating one example of the medical image diagnosis apparatus according to the first embodiment.

FIG. 5 illustrates the case where the medical image diagnosis apparatus 1 is an X-ray CT apparatus, an MRI apparatus, or the like. In this case, for example, the imaging unit 12 includes a gantry that is not illustrated and a couch device 127.

In the X-ray CT apparatus or the MRI apparatus, for example, the ultraviolet light source 22 is provided to the couch device 127. For example, a plurality of the ultraviolet light sources 22 are attached to a lower surface of an upper part of the couch device 127 as illustrated in FIG. 5. Here, each ultraviolet light source 22 may be attached so as to deliver the ultraviolet ray in a direction from the couch device 127 to the floor surface.

The irradiation controlling function 104b controls the irradiation of the irradiation object with the ultraviolet ray by moving the holder (couch device 127) that holds the ultraviolet light source 22 in a vertical direction so as to change the position of the ultraviolet light source 22 with respect to the irradiation object.

For example, as illustrated in FIG. 5, the irradiation controlling function 104b controls the couch device 127 so as to change the height of the couch device in the vertical direction. Here, the irradiation controlling function 104b transmits the control signal to the irradiation control unit 20 so that the ultraviolet light source 22 emits the ultraviolet ray. For example, the irradiation controlling function 104b transmits the control signal to the irradiation control unit 20 so that the ultraviolet ray is delivered while the height of the couch device 127 is changed. Thus, the ultraviolet ray is delivered to the lower part of the couch device 127 and the floor surface around the couch device 127.

In the description of the medical image diagnosis apparatus 1 with reference to FIG. 2 to FIG. 5, the position of the ultraviolet light source 22 with respect to the irradiation object is moved relatively by moving the holder that holds the ultraviolet light source 22. In the description made with reference to FIG. 6, the position of the ultraviolet light source 22 with respect to the irradiation object is changed relatively by moving the irradiation object. Note that in FIG. 6, the irradiation object is moved in the X-ray diagnosis apparatus illustrated in FIG. 3.

Figure 6:
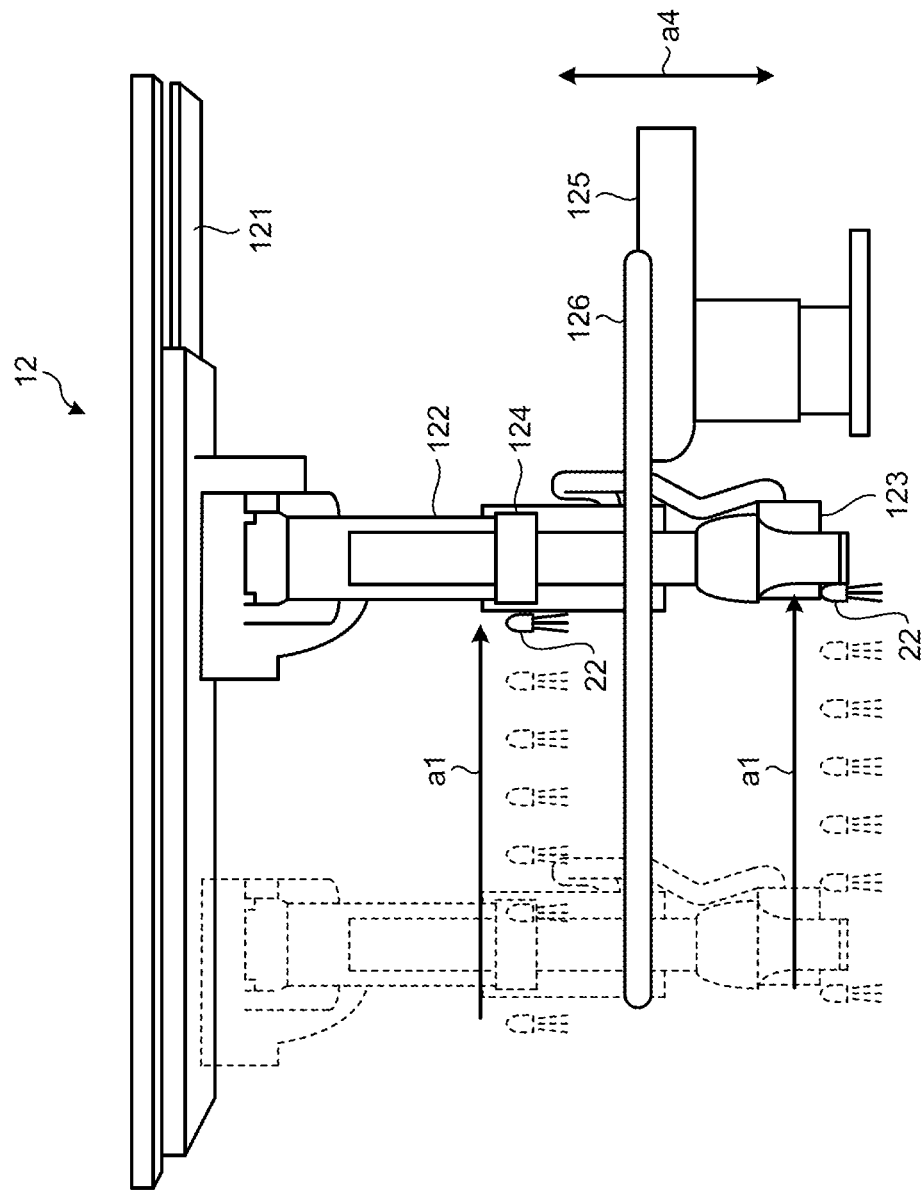
FIG. 6 is a diagram illustrating one example of the medical image diagnosis apparatus according to the first embodiment.

For example, the irradiation controlling function 104b controls the couch device 125 so that the height of the couch device 125 in the vertical direction is changed as illustrated by an arrow a4 in FIG. 6. In addition, the irradiation controlling function 104b not just changes the height of the couch device 125 in the vertical direction but also slides the couchtop 126 in a longitudinal direction and a lateral direction and controls the tilt of the couchtop 126 in the longitudinal direction and the lateral direction of the couchtop 126.

The irradiation controlling function 104b transmits the control signal to the irradiation control unit 20 so that the ultraviolet ray is delivered while the height of the couch device 125 is changed, while the couchtop 126 is moved, or while the couchtop 126 is tilted. Thus, the ultraviolet ray is delivered to the couch device 125 and the couchtop 126.

Furthermore, the irradiation controlling function 104b can control the irradiation of the irradiation object with the ultraviolet ray by combining the movement of the holder that holds the ultraviolet light source 22 and the movement of the irradiation object. For example, the irradiation controlling function 104b transmits the control signal to the irradiation control unit 20 so that the ultraviolet ray is delivered while controlling the slide of the C-arm 122 in the direction of the arrow a1 and the movement of the couch device 125 and the couchtop 126 as illustrated in FIG. 6. Thus, the irradiation controlling function 104b can deliver the ultraviolet ray in the wider range as compared to the case where only one of the movement of the holder that holds the ultraviolet light source 22 and the movement of the irradiation object is performed.

In the first embodiment described above, the processing circuitry 104, the system control circuitry 11, the irradiation control unit 20, and the light source control circuitry 21 may be viewed as a single unit and regarded as a "processing circuitry".

As described above, in the first embodiment, the ultraviolet light source 22 emits the ultraviolet ray. The irradiation controlling function 104b controls the irradiation of the irradiation object with the ultraviolet ray by moving the position of the ultraviolet light source 22 relatively with respect to the irradiation object irradiated with the ultraviolet ray in the examination room. Therefore, the medical image diagnosis apparatus 1 according to the first embodiment can eliminate the variation in cleanness or the cleaning failure resulting from manual wiping, and can perform sterilization frequently; thus, the stable hygiene management can be achieved.

The medical image diagnosis apparatus 1 according to the first embodiment, by using the ultraviolet ray, can reduce the use frequency of the disinfectant, reduce the risk of increasing the drug resistance of the bacteria, and also eliminate the bacteria. Moreover, the medical image diagnosis apparatus 1 according to the first embodiment can reduce the frequency of use of the disinfectant and manual wiping, thereby reducing the costs. In addition, by reducing the frequency of manual wiping, the medical image diagnosis apparatus 1 according to the first embodiment allows the worker who used to be engaged in wiping to be assigned to other tasks, making the examination work more efficient.

In the first embodiment, the irradiation controlling function 104b controls the irradiation of the irradiation object with the ultraviolet ray by moving the holder that holds the ultraviolet light source 22 so as to change the position of the ultraviolet light source 22 with respect to the irradiation object. Therefore, the medical image diagnosis apparatus 1 according to the first embodiment enables the easy irradiation of the irradiation object with the ultraviolet ray.

In the first embodiment, the irradiation controlling function 104b controls the irradiation of the irradiation object with the ultraviolet ray by moving the irradiation object so as to change the position of the ultraviolet light source with respect to the irradiation object. Thus, even when the ultraviolet light source 22 is fixed, the medical image diagnosis apparatus 1 according to the first embodiment can irradiate the irradiation object with the ultraviolet ray.

In the first embodiment, the irradiation controlling function 104b controls the irradiation of the irradiation object with the ultraviolet ray by moving the irradiation object in addition to the holder that holds the ultraviolet light source 22 so as to change the position of the ultraviolet light source 22 relatively with respect to the irradiation object. Therefore, the medical image diagnosis apparatus 1 according to the first embodiment can deliver the ultraviolet ray in the wider range.

In the first embodiment, the ultraviolet light source 22 is provided to at least one of the imaging unit and the couch where the subject is placed. The irradiation controlling function 104b moves the position of the ultraviolet light source 22 by operating at least one of the imaging unit and the couch where the subject is placed. Therefore, the medical image diagnosis apparatus 1 according to the first embodiment enables the irradiation with the ultraviolet ray using the movable part of the apparatus.

In the first embodiment, the ultraviolet light source 22 includes the light-emitting elements 22a. Therefore, the medical image diagnosis apparatus 1 according to the first embodiment can irradiate various irradiation objects with the suitable ultraviolet ray.

In the first embodiment, the light-emitting elements 22a are disposed densely. Therefore, the medical image diagnosis apparatus 1 according to the first embodiment can concentrate the light quantity of the ultraviolet rays.

In the first embodiment, the light-emitting elements 22a are disposed with the gap with the predetermined size between the adjacent light generators. For example, the light-emitting elements 22a are disposed in the ring shape. Therefore, the medical image diagnosis apparatus 1 according to the first embodiment can deliver the ultraviolet ray in the wider range. As a result, the shadow when the ultraviolet ray is delivered can be minimized.

Second Embodiment

Described in the first embodiment is the case where the ultraviolet light source 22 is directly attached to the movable part of the apparatus, for example, to the C-arm or the couch device, and the ultraviolet ray is delivered while the position of the ultraviolet light source 22 with respect to the irradiation object is changed by operating the movable part. In a second embodiment, the holder for holding the ultraviolet light source 22 is newly provided.

Figure 7:
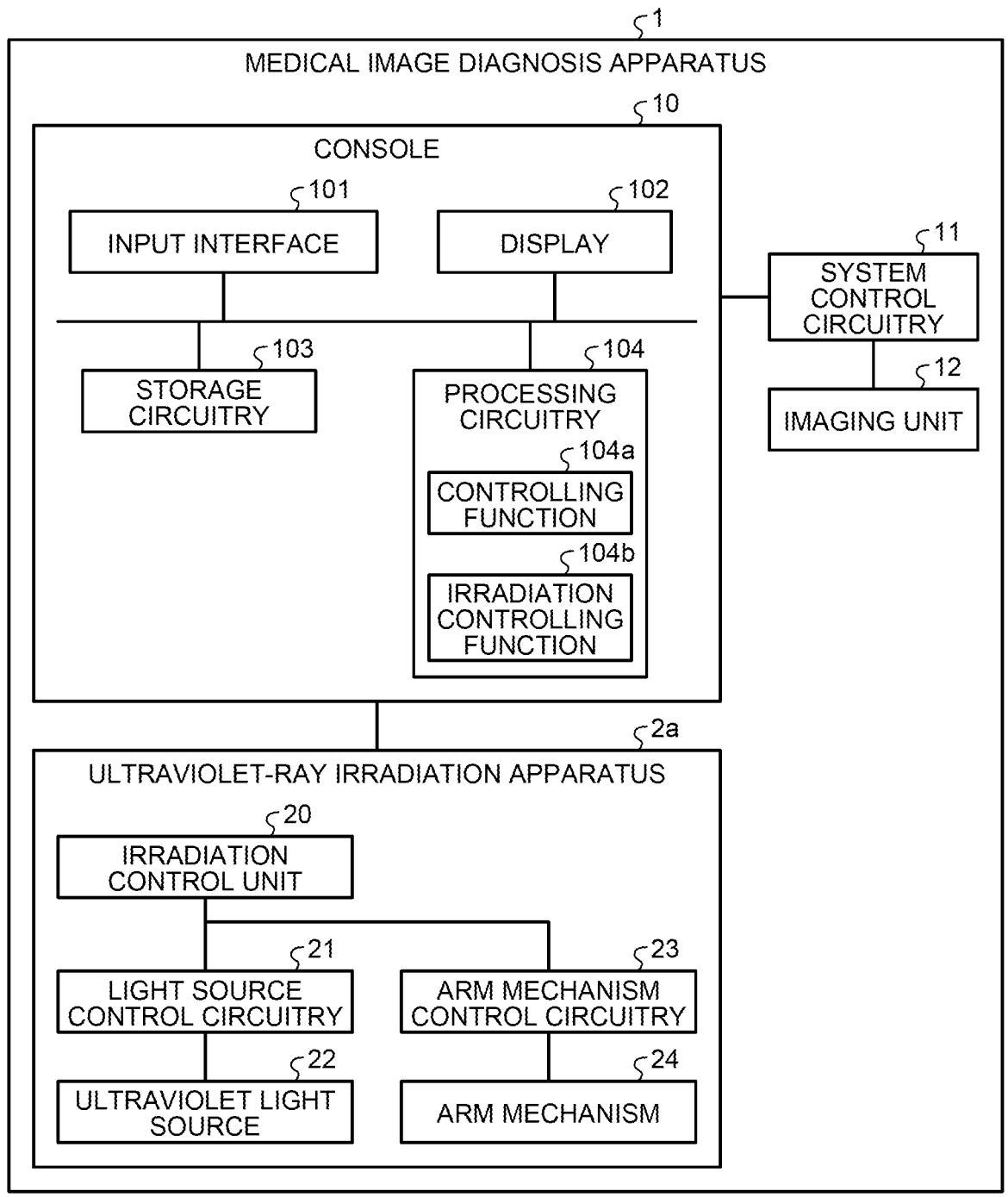
FIG. 7 is a diagram illustrating one example of a configuration of a medical image diagnosis apparatus according to a second embodiment.

FIG. 7 is a diagram illustrating one example of a configuration of the medical image diagnosis apparatus 1 according to the second embodiment. Note that the medical image diagnosis apparatus 1 and an ultraviolet-ray irradiation apparatus 2a according to the second embodiment are different from the medical image diagnosis apparatus 1 and the ultraviolet-ray irradiation apparatus 2 according to the first embodiment in the process by the irradiation controlling function 104b, the process by the irradiation control unit 20, and the new provision of arm mechanism control circuitry 23 and an arm mechanism. The following descriptions focus on these differences.

As illustrated in FIG. 7, the ultraviolet-ray irradiation apparatus 2a according to the second embodiment includes the arm mechanism control circuitry 23 and an arm mechanism 24.

The arm mechanism 24 includes an arm part and a movable part. The arm part holds the ultraviolet light source 22. Specifically, the arm part includes an attachment region where the ultraviolet light source 22 is attached by the attachment part 22b. Then, the arm part holds the ultraviolet light source 22 by the attachment of the ultraviolet light source 22 through the attachment region.

The movable part includes a driving mechanism such as a motor or an actuator, and moves the arm part by moving in accordance with the control received from the arm mechanism control circuitry 23. For example, the movable part achieves sliding operation, turning operation, bending operation, expanding and contracting operation, and the like by the driving mechanism.

The arm mechanism control circuitry 23 controls the operation of the arm mechanism 24 on the basis of the control signal received from the irradiation control unit 20. Specifically, the arm mechanism control circuitry 23 controls the sliding operation, turning operation, and bending operation of the arm mechanism 24 by operating the driving mechanism in the movable part of the arm mechanism 24 on the basis of the control signal received from the irradiation control unit.

The irradiation control unit 20 according to the second embodiment controls the arm mechanism control circuitry 23 in addition to the control of the light source control circuitry 21 described in the first embodiment. Specifically, the irradiation control unit controls the operation of the arm mechanism 24 on the basis of the control signal received from the medical image diagnosis apparatus 1. For example, the irradiation control unit 20 controls the arm mechanism control circuitry 23 by transmitting the control signal to the arm mechanism control circuitry 23, and controls the sliding operation, turning operation, and bending operation of the arm mechanism 24.

Figure 8:
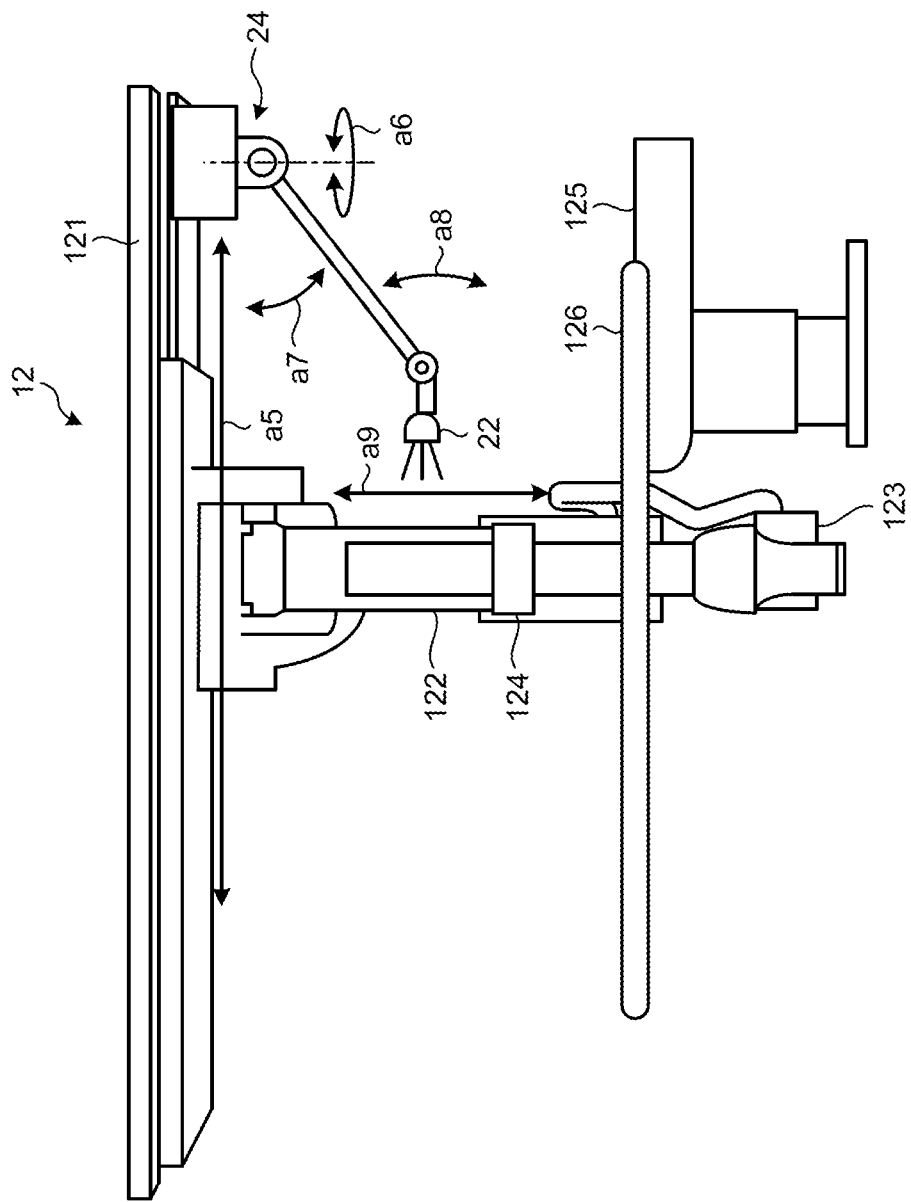
FIG. 8 is a diagram illustrating one example of the medical image diagnosis apparatus according to the second embodiment.

FIG. 8 to FIG. 12 are diagrams illustrating examples of the medical image diagnosis apparatus 1 according to the second embodiment. In FIG. 8, the medical image diagnosis apparatus 1 is the X-ray diagnosis apparatus equipped with the C-arm. The imaging unit 12 in the X-ray diagnosis apparatus according to the second embodiment includes the ceiling travel rail 121, the C-arm 122, the X-ray tube 123, the X-ray detector 124, and the couch device 125 including the couchtop 126.

In addition, the X-ray diagnosis apparatus includes the arm mechanism 24 at the ceiling travel rail 121. As illustrated in FIG. 8, the arm mechanism 24 includes a plurality of arm parts and a plurality of movable parts, and holds the ultraviolet light source 22 at an end of the arm mechanism.

The irradiation controlling function 104b according to the second embodiment operates the arm mechanism 24 by transmitting the control signal and the positional data to the irradiation control unit 20 so as to move the position of the ultraviolet light source 22 with respect to the irradiation object irradiated with the ultraviolet ray.

For example, by transmitting the control signal and the positional data to the irradiation control unit 20, the irradiation controlling function 104b performs the sliding operation in a direction of an arrow a5 along the ceiling travel rail 121, the turning operation in a direction of an arrow a6, the bending operation in directions of an arrow a7 and an arrow a8, and the sliding operation in a direction of an arrow a9 achieved by combining the sliding operation and the bending operation as illustrated in FIG. 8. Thus, the ultraviolet light source 22 held by the arm mechanism 24 is moved and the position of the ultraviolet light source 22 with respect to the irradiation object irradiated with the ultraviolet ray (for example, C-arm 122 or couchtop 126) is changed.

Here, the irradiation controlling function 104b controls the operation of the arm mechanism 24 on the basis of the positional data of the C-arm 122 and the couch device 125 and the positional data of the arm mechanism 24 so that the interference therebetween is avoided. For example, the irradiation controlling function 104b acquires the positional data of the arm mechanism 24 in the coordinate system of the X-ray diagnosis apparatus from the three-dimensional shape data of the arm mechanism 24 and the state of the movable part of the arm mechanism 24. Then, the irradiation controlling function 104b controls the movement of the arm mechanism 24 on the basis of the positional data of the C-arm 122 and the couch device 125 and the acquired positional data of the arm mechanism 24 so that the arm mechanism 24 does not interfere with the C-arm 122 or the couch device 125.

The irradiation controlling function 104b determines the irradiation position of the ultraviolet light source 22 on the basis of the positional data of the C-arm 122 and the couch device 125 and the positional data of the arm mechanism 24. For example, the irradiation controlling function 104b calculates the moving distance of the arm mechanism 24 where the distance from the emission surface of the ultraviolet ray to the irradiation object becomes the distance that is set in advance, on the basis of the respective pieces of positional data. Then, the irradiation controlling function 104b controls so that the ultraviolet light source 22 moves in the state where the arm mechanism 24 is moved on the basis of the calculated moving quantity and the distance from the emission surface of the ultraviolet ray to the irradiation object is kept. That is to say, the irradiation controlling function 104b controls the arm mechanism 24 so that the ultraviolet light source 22 moves in the state where the distance from the emission surface of the ultraviolet ray to the irradiation object is kept by combining various kinds of operation of the arm mechanism 24.

In addition, the irradiation controlling function 104b causes the ultraviolet light source 22 to emit the ultraviolet ray by transmitting the control signal to the irradiation control unit 20. For example, the irradiation controlling function 104b transmits the control signal to the irradiation control unit 20 so that the ultraviolet ray is delivered while the ultraviolet light source 22 is moved in the state where the distance from the emission surface of the ultraviolet ray to the irradiation object is kept. Thus, the irradiation object is irradiated with the ultraviolet ray.

Figure 9:
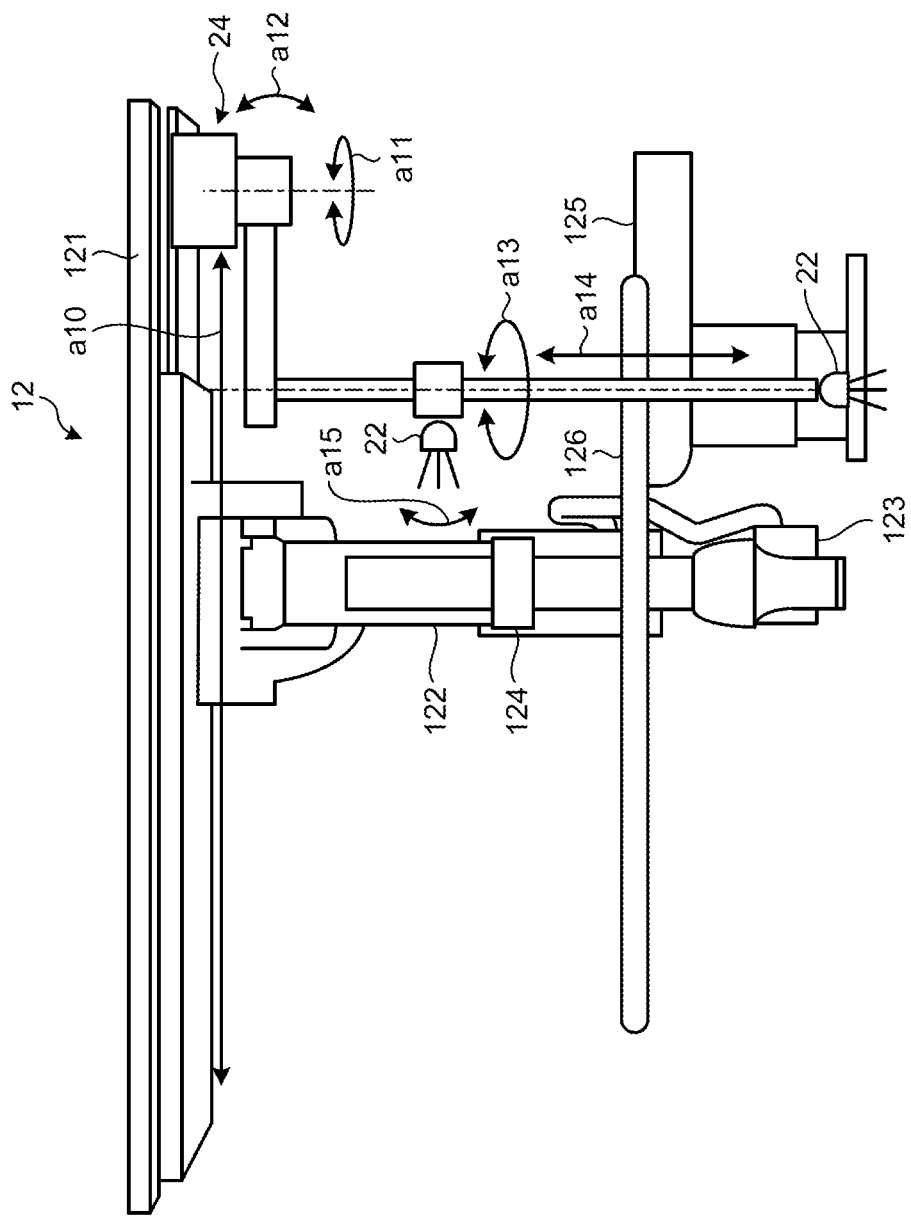
FIG. 9 is a diagram illustrating one example of the medical image diagnosis apparatus according to the second embodiment.

FIG. 9 illustrates another example of the arm mechanism 24 in the case where the medical image diagnosis apparatus 1 is the X-ray diagnosis apparatus equipped with the C-arm. For example, the X-ray diagnosis apparatus includes the arm mechanism 24 at the ceiling travel rail 121 as illustrated in FIG. 9. Then, the arm mechanism 24 includes a plurality of arm parts and a plurality of movable parts, and holds a plurality of the ultraviolet light sources 22.

For example, by transmitting the control signal and the positional data to the irradiation control unit 20, the irradiation controlling function 104b performs the sliding operation in a direction of an arrow a10 along the ceiling travel rail 121, the turning operation in directions of an arrow a11 and an arrow a13, the bending operation in directions of an arrow a12 and an arrow a15, and the expanding and contracting operation in a direction of an arrow a14 as illustrated in FIG. 9. Thus, the ultraviolet light source 22 held by the arm mechanism 24 is moved so that the positions of the ultraviolet light sources 22 with respect to the irradiation object irradiated with the ultraviolet ray (for example, C-arm 122, couchtop 126, and floor surface) are changed.

The irradiation controlling function 104b controls the irradiation with the ultraviolet ray by moving the ultraviolet light sources 22 in the state where the distance from the emission surface of the ultraviolet ray to the irradiation object is kept to be the distance that is set in advance while avoiding the interference on the basis of the positional data of the C-arm 122 and the couch device 125 and the positional data of the arm mechanism 24. Here, the irradiation controlling function 104b determines the irradiation position of each ultraviolet light source 22, and controls the irradiation of the irradiation object with the ultraviolet ray.

Figure 10:
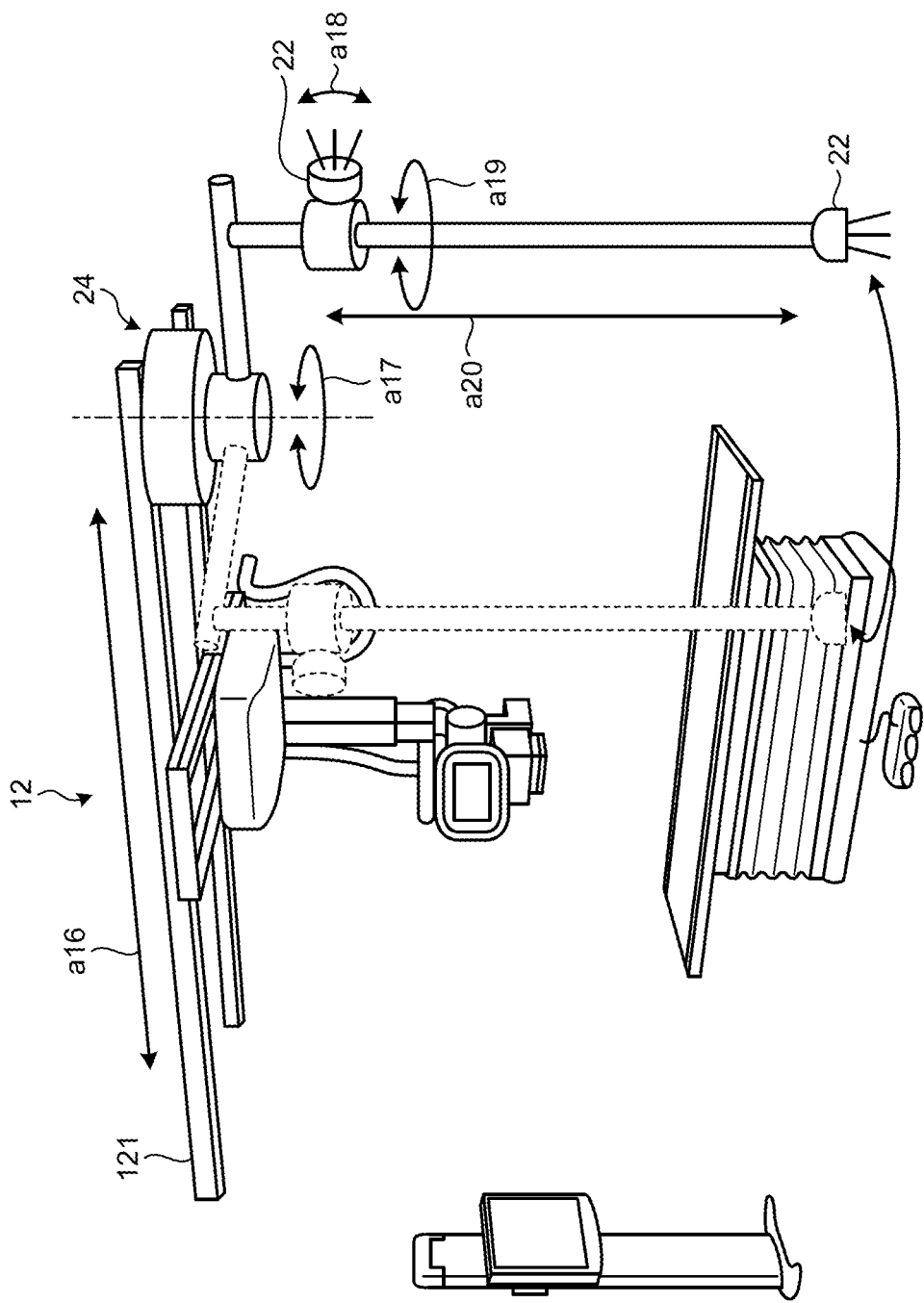
FIG. 10 is a diagram illustrating one example of the medical image diagnosis apparatus according to the second embodiment.

FIG. 10 illustrates the example of the arm mechanism 24 in the case where the medical image diagnosis apparatus 1 is the X-ray diagnosis apparatus performing general X-ray photographing. For example, the X-ray diagnosis apparatus includes the arm mechanism 24 at the ceiling travel rail 121 as illustrated in FIG. 10. The arm mechanism 24 includes the arm parts and the movable parts, and holds the ultraviolet light sources 22.

For example, by transmitting the control signal and the positional data to the irradiation control unit 20, the irradiation controlling function 104b performs the sliding operation in a direction of an arrow a16 along the ceiling travel rail 121, the turning operation in directions of an arrow a17 and an arrow a19, the bending operation in a direction of an arrow a18, and the expanding and contracting operation in a direction of an arrow a20 as illustrated in FIG. 10. Thus, the ultraviolet light sources 22 held by the arm mechanism 24 are moved so that the positions of the ultraviolet light sources 22 with respect to the irradiation object irradiated with the ultraviolet ray (for example, X-ray irradiation unit, X-ray detector, couch device, and floor surface) are changed.

Then, the irradiation controlling function 104b controls the irradiation with the ultraviolet ray by moving the ultraviolet light sources 22 in the state where the distance from the emission surface of the ultraviolet ray to the irradiation object is kept to be the distance that is set in advance while avoiding the interference on the basis of the positional data of the X-ray irradiation unit, the X-ray detector, and the couch device, and the positional data of the arm mechanism 24. Here, the irradiation controlling function 104b determines the irradiation position of each ultraviolet light source 22, and controls the irradiation of the irradiation object with the ultraviolet ray.

As described above, FIG. 8 to FIG. 10 illustrate the case where the arm mechanism 24 holding the ultraviolet light source 22 is provided on the X-ray diagnosis apparatus, and the irradiation with the ultraviolet ray is performed using the ultraviolet light source 22 by moving the arm mechanism 24. However, even in the case of providing the arm mechanism 24 holding the ultraviolet light source 22, the irradiation with the ultraviolet ray can be performed while changing the relative positional relation between the ultraviolet light source 22 and the irradiation object by moving the irradiation object. For example, in the X-ray diagnosis apparatus in FIG. 8 and FIG. 9, the irradiation with the ultraviolet ray is performed by operating the C-arm 122 or the couchtop 126 with the position of the arm mechanism 24 fixed so as to change the position of the C-arm 122 or the couchtop 126 with respect to the ultraviolet light source 22. Moreover, for example, in the X-ray diagnosis apparatus in FIG. 10, the irradiation with the ultraviolet ray is performed by moving the X-ray irradiation unit traveling on the ceiling travel rail 121 while the position of the arm mechanism 24 is fixed so as to change the position of the X-ray irradiation unit with respect to the ultraviolet light source 22.

Figure 11:
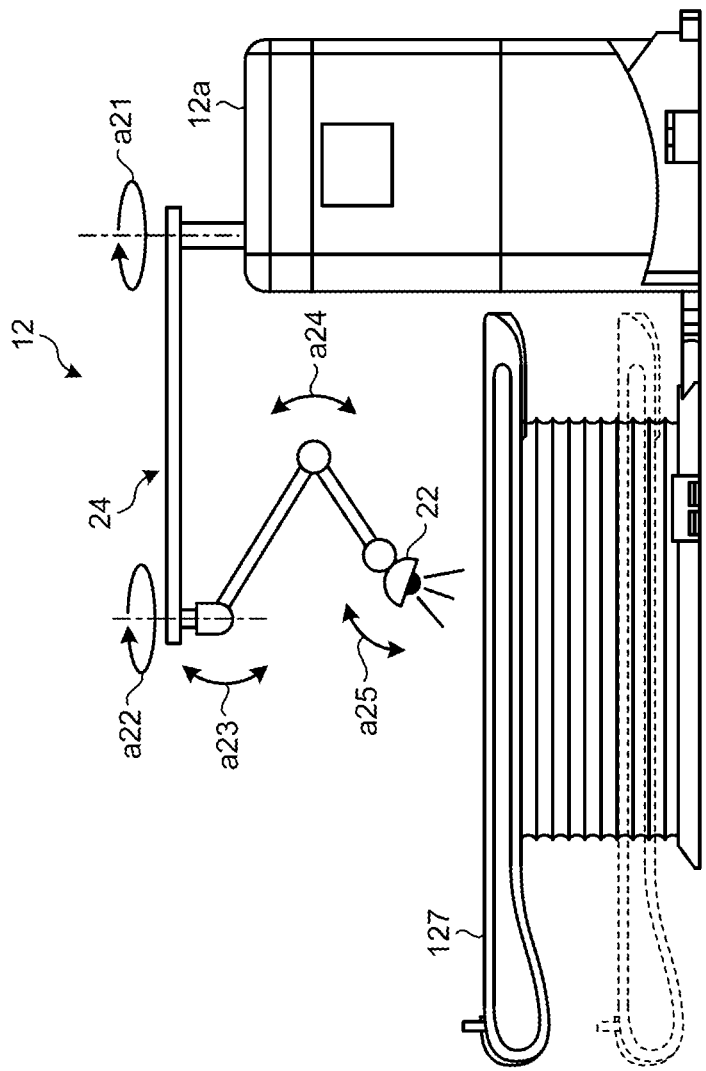
FIG. 11 is a diagram illustrating one example of the medical image diagnosis apparatus according to the second embodiment.

FIG. 11 illustrates the case where the medical image diagnosis apparatus 1 is the X-ray CT apparatus, the MRI apparatus, or the like. In this case, for example, the imaging unit 12 includes a gantry 12a and the couch device 127.

The X-ray CT apparatus or the MRI apparatus includes, for example, the arm mechanism 24 on the gantry 12a. This arm mechanism 24 includes the arm parts and the movable parts, and holds the ultraviolet light source 22 at an end of the arm mechanism as illustrated in FIG. 11.

By transmitting the control signal and the positional data to the irradiation control unit 20, the irradiation controlling function 104b performs the turning operation in directions of an arrow a21 and an arrow a22, the bending operation in directions of an arrow a23 to an arrow a25, and the like as illustrated in FIG. 11. Thus, the ultraviolet light source 22 held by the arm mechanism 24 is moved and the position of the ultraviolet light source 22 with respect to the irradiation object irradiated with the ultraviolet ray (for example, couch device 127) is changed.

Here, the irradiation controlling function 104b controls the operation of the arm mechanism 24 so as to avoid the interference on the basis of the positional data of the gantry 12a and the couch device 127 and the positional data of the arm mechanism 24. For example, the irradiation controlling function 104b acquires the positional data of the arm mechanism 24 in the coordinate system of the medical image diagnosis apparatus from the three-dimensional shape data of the arm mechanism 24 and the state of the movable part of the arm mechanism 24. Then, the irradiation controlling function 104b controls the movement of the arm mechanism so that the arm mechanism 24 does not interfere with the gantry 12a or the couch device 127 on the basis of the positional data of the gantry 12a and the couch device 127 and the acquired positional data of the arm mechanism 24.

In addition, the irradiation controlling function 104b determines the irradiation position of the ultraviolet light source 22 on the basis of the positional data of the gantry 12a and the couch device 127 and the positional data of the arm mechanism 24. For example, the irradiation controlling function 104b calculates the moving quantity of the arm mechanism 24 to make the distance from the emission surface of the ultraviolet ray to the irradiation object become the distance set in advance, on the basis of the positional data. Then, the irradiation controlling function 104b controls the arm mechanism 24 to move on the basis of the calculated moving quantity, and controls the ultraviolet light source 22 to move while maintaining the distance from the emission surface of the ultraviolet ray to the irradiation object. That is to say, the irradiation controlling function 104b controls the arm mechanism 24 so that the ultraviolet light source 22 moves in the state where the distance from the emission surface of the ultraviolet ray to the irradiation object is kept by combining various kinds of operation of the arm mechanism 24.

Furthermore, the irradiation controlling function 104b causes the ultraviolet light source 22 to emit the ultraviolet ray by transmitting the control signal to the irradiation control unit 20. For example, the irradiation controlling function 104b transmits the control signal to the irradiation control unit 20 so that the ultraviolet ray is delivered while the ultraviolet light source 22 is moved in the state where the distance from the emission surface of the ultraviolet ray to the irradiation object is kept. Thus, the irradiation object such as the couch device 127 is irradiated with the ultraviolet ray.

Figure 12:
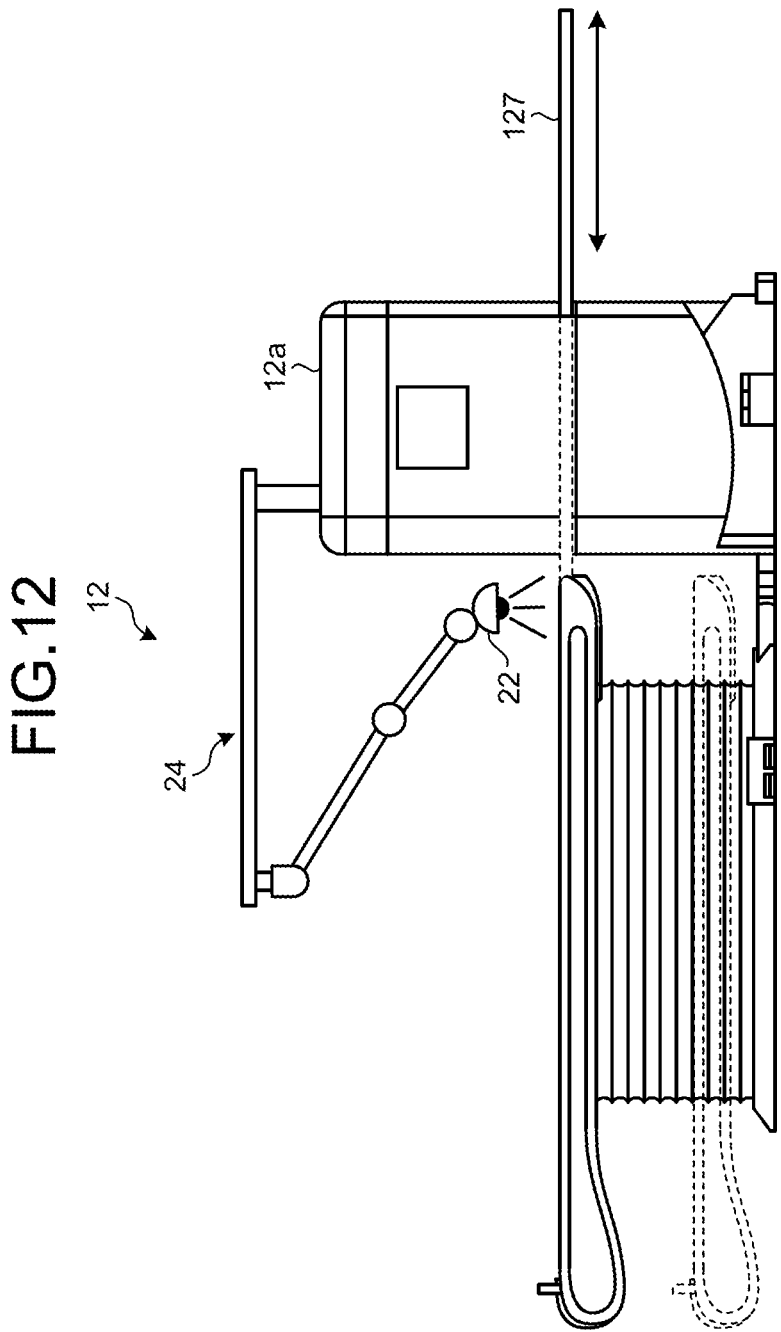
FIG. 12 is a diagram illustrating one example of the medical image diagnosis apparatus according to the second embodiment.

Next, with reference to FIG. 12, description is made of the case where the position of the ultraviolet light source 22 is changed relatively with respect to the irradiation object by moving the irradiation object. Note that FIG. 12 illustrates the case where the irradiation object is moved in the medical image diagnosis apparatus illustrated in FIG. 11.

For example, the irradiation controlling function 104b controls the couch device 125 so that the couchtop of the couch device 127 slides in the longitudinal direction as illustrated in FIG. 12. In addition, the irradiation controlling function 104b controls the change of the height of the couch device 127 in the vertical direction.

Then, the irradiation controlling function 104b transmits the control signal to the irradiation control unit 20 so that the ultraviolet ray is delivered while the couchtop is moved or while the height of the couch device 127 is changed. That is to say, the irradiation controlling function 104b irradiates the irradiation object with the ultraviolet ray by changing the position of the couchtop or the like while the ultraviolet ray is delivered with the position of the ultraviolet light source 22 fixed.

Moreover, the irradiation controlling function 104b can control the irradiation of the irradiation object with the ultraviolet ray by combining the movement of the arm mechanism 24 holding the ultraviolet light source 22 and the movement of the irradiation object. For example, in the X-ray diagnosis apparatus illustrated in FIG. 8, the irradiation controlling function 104b transmits the control signal to the irradiation control unit 20 so that the ultraviolet ray is delivered while controlling the movement of the arm mechanism holding the ultraviolet light source 22 and the slide of the C-arm 122.

As described above, in the second embodiment, the case where the holder (arm mechanism 24) holding the ultraviolet light source 22 is newly provided has been described. Here, the irradiation of the irradiation object with the ultraviolet ray in the second embodiment may be combined with the irradiation of the irradiation object with the ultraviolet ray described in the first embodiment. That is to say, the arm mechanism 24 may be disposed in the medical image diagnosis apparatus 1 according to the first embodiment in which the ultraviolet light source 22 is provided directly to the movable part of the apparatus and by operating the movable part, the irradiation object is irradiated with the ultraviolet ray. In this case, the irradiation controlling function 104b can combine the control described in the first embodiment and the control described in the second embodiment as appropriate.

In the aforementioned second embodiment, the processing circuitry 104, the system control circuitry 11, the irradiation control unit 20, the light source control circuitry 21, and the arm mechanism control circuitry 23 may be viewed as a single unit and regarded as "processing circuitry".

As described above, in the second embodiment, the arm mechanism 24 holds the ultraviolet light source 22. The irradiation controlling function 104b controls the arm mechanism 24 so as to control the position of the ultraviolet light source 22, and thus, the irradiation object is irradiated with the ultraviolet ray. Therefore, by providing the arm mechanism 24 at the arbitrary position, the medical image diagnosis apparatus 1 according to the second embodiment can deliver the ultraviolet ray in the wider range and the more stable hygiene management can be achieved.

Third Embodiment

In the first embodiment and the second embodiment, the method of delivering the ultraviolet ray has been described. In a third embodiment, setting of the timing of performing a sterilization process by the ultraviolet-ray irradiation and the irradiation range are described. That is to say, the third embodiment describes the setting of the timing of performing the sterilization process by the ultraviolet-ray irradiation and the irradiation range in the medical image diagnosis apparatus 1 in the first embodiment and the second embodiment.

Figure 13:
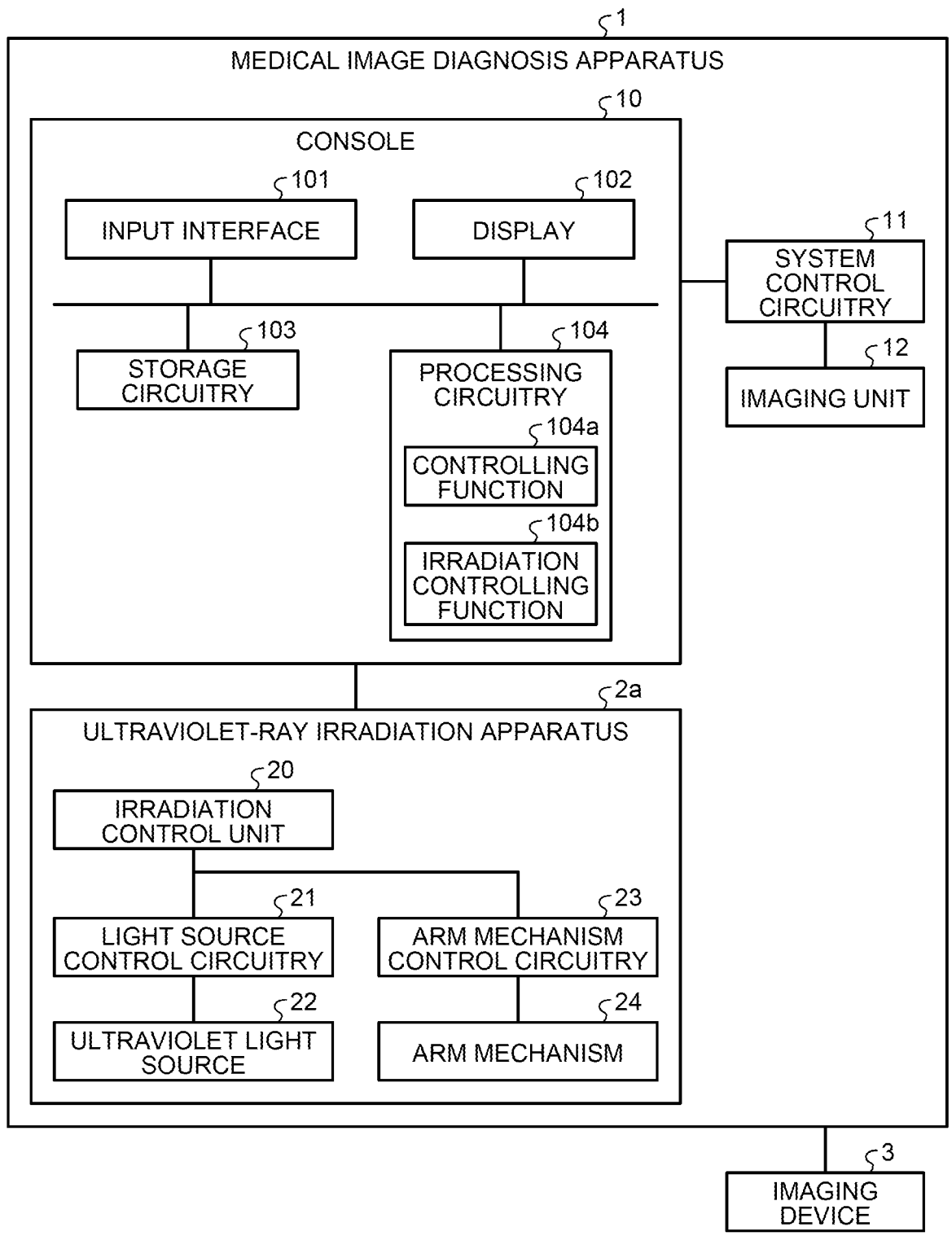
FIG. 13 is a diagram illustrating one example of a configuration of a medical image diagnosis apparatus according to a third embodiment.

FIG. 13 is a diagram illustrating one example of a configuration of the medical image diagnosis apparatus 1 according to the third embodiment. Note that the medical image diagnosis apparatus 1 according to the third embodiment is different from the medical image diagnosis apparatus 1 according to the second embodiment in the process by the irradiation controlling function 104b, the information stored in the storage circuitry 103, and the connection of an imaging device 3. The following descriptions focus on these differences.

As illustrated in FIG. 13, the medical image diagnosis apparatus 1 according to the third embodiment is connected to the imaging device 3. The imaging device 3 is disposed in the examination room where the medical image diagnosis apparatus 1 is disposed, and acquires the image data or the shape data in the examination room. For example, the imaging device 3 is a compound eye camera or a three-dimensional scanner, and acquires the three-dimensional image data or shape data in the examination room and transmits the acquired three-dimensional image data or shape data to the processing circuitry 104.

The storage circuitry 103 according to the third embodiment stores various kinds of information for setting the timing of performing the sterilization process and the irradiation range. For example, the storage circuitry 103 stores therein a plurality of pieces of preset information in which the timing of performing the sterilization process or the irradiation range are set.

For example, the storage circuitry 103 stores therein the preset information in which "nighttime (outside working hours)", "before examination", "after examination", "custom (for example, designated time)", or the like is defined as the timing of performing the sterilization process. In addition, for example, the storage circuitry 103 stores therein the preset information in which "imaging unit", "couch device", "floor", "patient contact part (upper part of couch, opening of gantry)", "opening of gantry", "peripheral device or facility", or the like is defined as the irradiation range. Note that in the preset information, the timing of performing the sterilization process and the irradiation range may be correlated with each other.

The irradiation controlling function 104b according to the third embodiment specifies the irradiation range of the irradiation object, and controls the irradiation with the ultraviolet ray in the specified irradiation range. For example, on the basis of the preset information selected from the pieces of preset information in which the irradiation range is defined for at least one of the examination kind and the examination part, the irradiation controlling function 104b specifies the irradiation range for the irradiation object and controls the irradiation with the ultraviolet ray in the specified irradiation range. For example, the irradiation controlling function 104b selects the preset information corresponding to the timing of performing the sterilization process from the pieces of preset information stored in the storage circuitry 103, and controls the irradiation so as to deliver the ultraviolet ray to the irradiation range set in the selected preset information.

For example, based on the circumstance of the apparatus at the current time, the irradiation controlling function 104b determines whether the current time is the timing to perform the sterilization process and when it is determined that the current time is the timing of performing the sterilization process, the irradiation controlling function 104b selects the preset information corresponding to the timing of performing the sterilization process from the pieces of preset information, and based on the selected preset information, controls the irradiation with the ultraviolet ray. That is to say, the irradiation controlling function 104b compares the circumstance of the apparatus at the current time and the timing of performing the sterilization process in the pieces of preset information stored in the storage circuitry 103, and determines whether the current time is the timing of performing the sterilization process. Then, when the irradiation controlling function 104b determines that the current time is the timing of performing the sterilization process, the irradiation controlling function 104b reads out the information about the corresponding irradiation range and controls the irradiation with the ultraviolet ray in the read irradiation range.

For example, when the pieces of preset information include the preset information in which "timing of performing the sterilization process: nighttime (outside working hours)" and "irradiation range: imaging unit, couch device, floor" are correlated, the irradiation controlling function 104b determines that the nighttime is the timing of performing the sterilization process. Then, the irradiation controlling function 104b selects the preset information in which "timing of performing the sterilization process: nighttime (outside working hours)" and "irradiation range: imaging unit, couch device, floor" are correlated from among the pieces of preset information, and based on the selected preset information, the irradiation controlling function 104b delivers the ultraviolet ray to the irradiation object of "imaging unit", "couch device", and "floor".

Similarly, the irradiation controlling function 104b determines that the timing of "before examination", "after examination", or "designated time or the like" is the timing of performing the sterilization process on the basis of the circumstance of the apparatus at the current time. The irradiation controlling function 104b selects the corresponding preset information from among the pieces of preset information and controls the irradiation with the ultraviolet ray based on the selected preset information.

As described above about the irradiation range, the irradiation object includes the device and facility in the examination room. That is to say, the irradiation controlling function 104b can specify the irradiation range on the device and facility in the examination room, and control the irradiation with the ultraviolet ray in the specified irradiation range. Here, the positional information about "imaging unit", "couch device", "floor", and the like is acquired based on the positional data in the medical image diagnosis apparatus 1; however, the position of "peripheral device and facility" of the medical image diagnosis apparatus 1 cannot be acquired from the positional data in the medical image diagnosis apparatus 1. In view of this, the irradiation controlling function 104b automatically detects at least one of the device and facility from the examination room on the basis of the photographing result obtained by an optical photographing equipment disposed in the examination room. For example, the irradiation controlling function 104b acquires the position of "the peripheral device and facility" in the examination room on the basis of the three-dimensional image data or shape data in the examination room acquired by the imaging device 3 (optical photographing equipment).

For example, the irradiation controlling function 104b controls the imaging device 3 disposed in the examination room so as to acquire the three-dimensional image data or shape data in the examination room. The irradiation controlling function 104b specifies the position and the shape of the peripheral device and facility in the examination room on the basis of the acquired three-dimensional image data or shape data. Here, the irradiation controlling function 104b can use the light emitted from the ultraviolet light source 22 also as the illumination for the optical photographing. That is to say, the irradiation controlling function 104b detects automatically at least one of the device and the facility from the examination room on the basis of the photographing result obtained when the optical photographing equipment photographs the examination room that is illuminated with light emitted from the ultraviolet light source 22. Note that this light as the illumination may be ultraviolet light, visible light, or the light that extends over both wavelength regions. In the case of using the ultraviolet light as the illumination, the imaging device 3 may be formed by a camera device for ultraviolet light or may be a general camera device for visible light because the camera device for visible light usually has sensitivity in the ultraviolet wavelength region.

Note that in the case of using the visible light emitted from the ultraviolet light source 22 as the illumination, the visible light wavelength region of the light emitted from the light-emitting element 22a may be used or the light-emitting elements 22a may include the light-emitting element emitting the visible light. The aforementioned peripheral device and facility are, for example, an injector for injecting a contrast medium, an electrocardiograph, various terminals, and the like.

Then, the irradiation controlling function 104b calculates the irradiation route of the ultraviolet ray on the basis of the specified position and shape. For example, the irradiation controlling function 104b calculates the irradiation route for delivering the ultraviolet ray to the peripheral device or facility while avoiding the interference with another device on the basis of the positional data of other device than the irradiation object including the apparatus, the position and shape of the peripheral device or facility in the three-dimensional space of the examination room, and the movable range of the arm mechanism 24 that holds the ultraviolet light source 22. Here, the irradiation controlling function 104*b* calculates the irradiation route so that the distance from the emission surface of the ultraviolet ray to the peripheral device or facility becomes the distance set in advance. Then, the irradiation controlling function 104*b* irradiates the peripheral device or facility with the ultraviolet ray while changing the relative position between the emission surface of the ultraviolet ray and the peripheral device or facility in the state where the distance set in advance is kept on the basis of the calculated irradiation route.

In this manner, the irradiation controlling function 104*b* can automatically detect at least one of the device and facility in the examination room from the examination room, specify the irradiation range on the detected one of the device and facility in the examination room on the basis of the detection result, and control the irradiation with the ultraviolet ray in the specified irradiation range. Note that before the imaging device 3 acquires the three-dimensional image data or shape data of the peripheral device or facility, the examination room may be divided into a plurality of areas and the areas where the peripheral device and facility are disposed may be set in advance. In this case, the irradiation controlling function 104*b* acquires the three-dimensional image data or shape data of the area set in advance.

Here, the irradiation controlling function 104*b* can cause the storage circuitry 103 to store the specified shape of the peripheral device or facility and the calculated irradiation route therein. For example, the three-dimensional shape data of the peripheral device such as an injector or an electrocardiograph and the irradiation route calculated for the three-dimensional shape data are stored in the storage circuitry 103. Thus, in the case where the peripheral device or facility is not moved in the examination room, the irradiation controlling function 104*b* can perform the irradiation with the ultraviolet ray without specifying the shape and calculating the irradiation route again by reading out the stored information.

Described with the aforementioned example is the case where the ultraviolet ray is delivered to the irradiation range that is set in advance. Here, the irradiation range may be set in accordance with the examination kind or the examination part. For example, the irradiation range of the ultraviolet ray irradiation performed between the examinations may be set in accordance with the examination protocol used in the previous examination or the treatment plan.

For example, the place where the sterilization process is needed concentratedly depends on the event during the procedure, and the event in the procedure is related with the examination content; therefore, by reflecting the information about the examination protocol (examination part) in the previous examination or the treatment plan in the content of the sterilization process, the sterilization process can be performed more suitably. For example, in the case where the examination protocol is the head part, craniotomy may be carried out at the same time as interventional radiology (IVR); therefore, the irradiation may be concentratedly performed in the periphery of the head part of the couch in addition to the periphery of the sheath (insertion port to insert the catheter).

In this case, for example, the preset information about the irradiation range where "irradiation range: sheath periphery, couch head part periphery" is correlated with "examination protocol: head part" is stored in the storage circuitry 103. The irradiation controlling function 104*b* acquires the previous examination protocol at the timing of performing the sterilization process after the examination, refers to the preset information about the corresponding irradiation range from among the pieces of preset information on the basis of the acquired examination protocol, and performs the irradiation with the ultraviolet ray in accordance with the preset information that is referred to. Here, in the case where the acquired examination protocol is "head part", the irradiation controlling function 104*b* delivers the ultraviolet ray to the sheath periphery and the couch head part periphery in accordance with the preset information.

In addition, in the case where the examination protocol is the lower limbs, for example, the plantar artery may be needled; therefore, it may be set to focus irradiation on the proximity of the plantar part in addition to the sheath periphery. In this case, for example, the preset information about the irradiation range in which "irradiation range: sheath periphery, proximity of plantar part" is correlated with "examination protocol: lower limbs" is stored in the storage circuitry 103. In the case where the acquired examination protocol is "lower limbs", the irradiation controlling function 104*b* irradiates the sheath periphery and the proximity of the plantar part with the ultraviolet ray in accordance with the corresponding preset information.

The irradiation range may be set in accordance with the subject examined in the medical image diagnosis apparatus 1. For example, the irradiation range of the ultraviolet-ray irradiation performed between the examinations may be set in consideration of the infection risk of the subject that has been examined previously.

For example, the irradiation range may be set differently for the subject infected with the infectious disease and the subject not infected with the infectious disease. In one example, if the previously examined subject is not infected with the infectious disease, "the patient contact part" may be irradiated with the ultraviolet ray, and if the previously examined subject is infected with the infectious disease, "the entire examination room" may be irradiated with the ultraviolet ray.

In this case, for example, the preset information about the irradiation range in which "irradiation range: patient contact part" is correlated with "subject: without infectious disease" and "irradiation range: entire examination room" is correlated with "subject: with infectious disease" is stored in the storage circuitry 103. The irradiation controlling function 104*b* acquires the subject information of the subject examined previously, and determines whether the subject is infected with the infectious disease from the acquired subject information. Then, the irradiation controlling function 104*b* performs the irradiation with the ultraviolet ray on the basis of the determination result.

Described with the aforementioned example is the case where the position or shape of the peripheral device or facility is specified based on the three-dimensional image data or shape data acquired by the imaging device 3. The irradiation controlling function 104*b* can further detect the event in the procedure on the basis of the image data acquired by the imaging device 3 and set the irradiation range in accordance with the detection result.

For example, the irradiation controlling function 104*b* determines whether the event such as "craniotomy" has occurred in the procedure by collecting the video (image data) in the procedure by the imaging device 3 and analyzing the collected image data. Here, in the occurrence of the event such as "craniotomy", the irradiation controlling function 104b determines "couch head part periphery" as the irradiation range. These pieces of information can also be stored in the storage circuitry 103 as the preset information.

Figure 14:
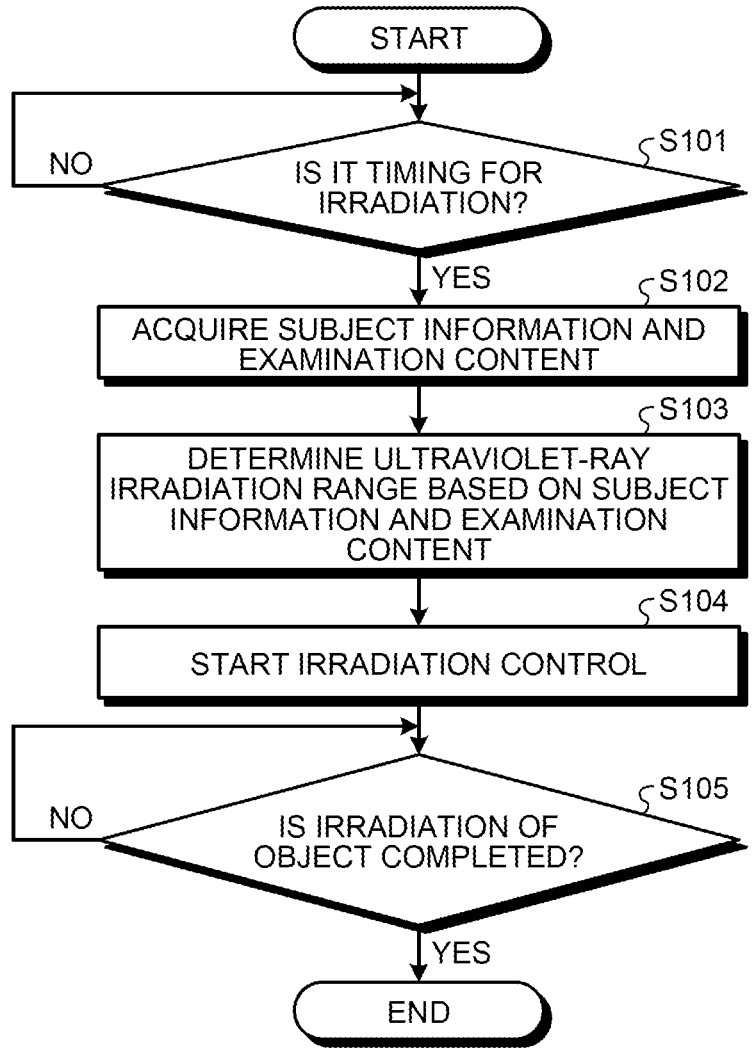
FIG. 14 is a flowchart for describing the procedure of the process of the medical image diagnosis apparatus 1 according to the third embodiment.

Next, with reference to FIG. 14, the process of the medical image diagnosis apparatus 1 according to the third embodiment is described. FIG. 14 is a flowchart for describing the procedure of the process of the medical image diagnosis apparatus 1 according to the third embodiment. Here, steps S101 to S105 in FIG. 14 are steps performed when the processing circuitry 104 reads out the computer program corresponding to the irradiation controlling function 104b from the storage circuitry 103 and executes the computer program.

As illustrated in FIG. 5, in the medical image diagnosis apparatus 1, first, the processing circuitry 104 determines whether it is the timing of performing the sterilization process with the ultraviolet ray (step S101). Here, if the processing circuitry 104 determines that it is the timing of performing the sterilization process (Yes at step S101), the processing circuitry 104 acquires the subject information and the examination content (step S102). Note that the medical image diagnosis apparatus 1 stands by until the timing of the sterilization process comes (No at step S101).

Then, the processing circuitry 104 determines the irradiation range of the ultraviolet ray on the basis of the subject information and the examination content (step S103). Then, the processing circuitry 104 starts the ultraviolet-ray irradiation control (step S104) and determines whether the irradiation of the irradiation object is completed (step S105).

Here, if the irradiation is completed (Yes at step S105), the processing circuitry 104 ends the irradiation with the ultraviolet ray. On the other hand, if the irradiation is not completed (No at step S105), the processing circuitry 104 continues the irradiation control.

As described above, in the third embodiment, the irradiation controlling function 104b specifies the irradiation range on the irradiation object and controls the irradiation with the ultraviolet ray in the specified irradiation range. Therefore, the medical image diagnosis apparatus 1 according to the third embodiment can set the irradiation range in accordance with the circumstance, and perform the stable hygiene management efficiently.

For example, in the case of performing the irradiation with the ultraviolet ray between the examinations, the sterilization process needs to be performed efficiently in the limited time. Therefore, by specifying the irradiation range where the irradiation with the ultraviolet ray is necessary for each time, the sterilization process can be performed more efficiently.

In the third embodiment, on the basis of the preset information selected from the pieces of preset information in which the irradiation range is defined for at least one of the examination kind and the examination part, the irradiation controlling function 104b specifies the irradiation range on the irradiation object and controls the irradiation with the ultraviolet ray in the specified irradiation range. Therefore, the medical image diagnosis apparatus 1 according to the third embodiment can set the irradiation range suitably.

In addition, in the third embodiment, the irradiation object includes the device and facility in the examination room. The irradiation controlling function 104b specifies the irradiation range on the device and facility in the examination room, and controls the irradiation with the ultraviolet ray in the specified irradiation range. Therefore, the medical image diagnosis apparatus 1 according to the third embodiment can irradiate not just the apparatus but also various devices and facilities in the examination room with the ultraviolet ray.

Furthermore, in the third embodiment, on the basis of at least one of the device and facility in the examination room included in the preset information selected from the pieces of preset information in which the irradiation range is defined, the irradiation controlling function 104b specifies the irradiation range on the device and facility in the examination room and controls the irradiation with the ultraviolet ray in the specified irradiation range. Therefore, the medical image diagnosis apparatus 1 according to the third embodiment can set the peripheral device or facility to become the irradiation object in advance.

In addition, in the third embodiment, the irradiation controlling function 104b automatically detects at least one of the device and facility from the examination room, specifies the irradiation range on the device and facility in the examination room on the basis of the detection result, and controls the irradiation with the ultraviolet ray in the specified irradiation range. Therefore, the medical image diagnosis apparatus 1 according to the third embodiment can irradiate the peripheral device or facility with the ultraviolet ray automatically.

Moreover, in the third embodiment, the irradiation controlling function 104b automatically detects at least one of the device and facility from the examination room on the basis of the photographing result obtained by the imaging device 3 disposed in the examination room. Therefore, the medical image diagnosis apparatus 1 according to the third embodiment can easily detect the peripheral device or facility automatically.

In the third embodiment, the irradiation controlling function 104b automatically detects at least one of the device and facility from the examination room on the basis of the photographing result obtained when the imaging device 3 photographs the examination room illuminated with the visible light emitted from the ultraviolet light source. Therefore, the medical image diagnosis apparatus 1 according to the third embodiment can acquire the information inside the examination room without preparing another illumination equipment.

In the third embodiment, the irradiation controlling function 104b generates the three-dimensional shape data about the device and facility in the examination room on the basis of the irradiation with the ultraviolet ray in the irradiation range on the device and facility in the examination room, and causes the storage circuitry 103 to store the generated three-dimensional shape data therein. Therefore, the medical image diagnosis apparatus 1 according to the third embodiment can omit the processes of specifying the shape of the peripheral device and facility and calculating the irradiation route.

Other Embodiments

The first embodiment to the third embodiment have been described so far; however, various other embodiments than the first embodiment to the third embodiment described above may be performed.

In the aforementioned embodiments, the X-ray diagnosis apparatus, the X-ray CT apparatus, and the MRI apparatus are employed as the examples of the medical image diagnosis apparatus 1; however, the embodiments are not limited to these examples and another medical image diagnosis apparatus such as a PET apparatus may be used as the medical image diagnosis apparatus 1.

Described with the aforementioned embodiments is the case where the processing circuitry 104, the system control circuitry 11, the irradiation control unit 20, the light source control circuitry 21, and the arm mechanism control circuitry 23 are included in the configuration, and these elements perform the respective processes; however, the embodiments are not limited to this example, and the processes performed by the respective configurations may be performed by one processing circuitry. For example, the processing circuitry 104 may be configured to collectively perform the processes that are performed by the system control circuitry 11, the irradiation control unit 20, the light source control circuitry 21, and the arm mechanism control circuitry 23. That is to say, the processing circuitry 104 may perform the controlling function that is described as being performed by the controlling function 104a, the irradiation controlling function 104b, and the system control circuitry 11, the controlling function that is described as being performed by the irradiation control unit 20, the controlling function that is described as being performed by the light source control circuitry 21, and the controlling function that is described as being performed by the arm mechanism control circuitry 23.

Described with the aforementioned embodiments is the case where the medical image diagnosis apparatus 1 controls the irradiation with the ultraviolet ray. However, the embodiments are not limited to this example and the ultraviolet-ray irradiation apparatus may control the aforementioned irradiation with the ultraviolet ray.

Figure 15:
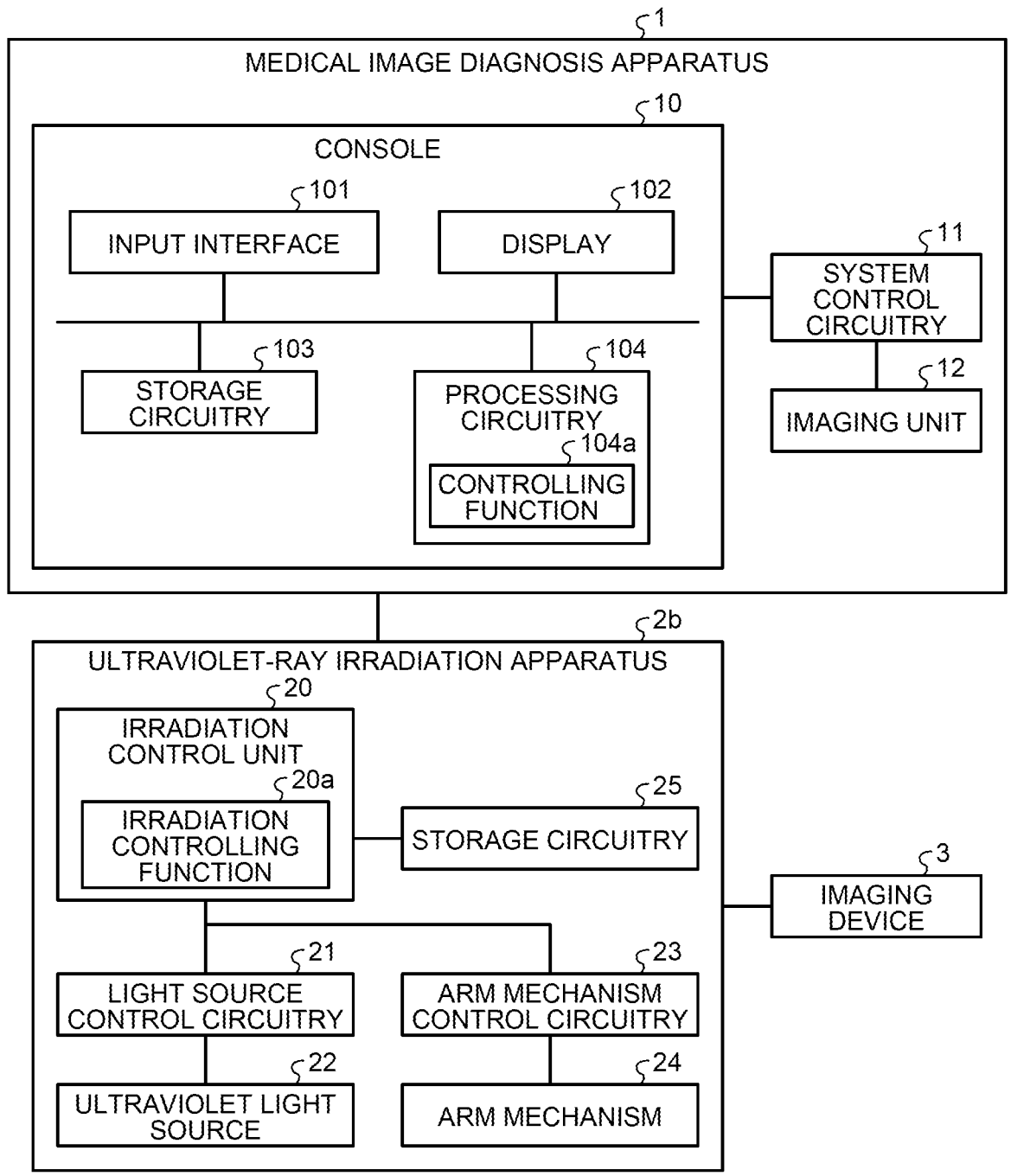
FIG. 15 is a diagram illustrating one example of a configuration of the ultraviolet-ray irradiation apparatus according to another embodiment.

FIG. 15 is a diagram illustrating one example of the configuration of the ultraviolet-ray irradiation apparatus according to another embodiment. An ultraviolet-ray irradiation apparatus 2b according to the other embodiment includes, as illustrated in FIG. 15, the irradiation control unit 20, the light source control circuitry 21, the ultraviolet light source 22, the arm mechanism control circuitry 23, the arm mechanism 24, and storage circuitry 25, and is connected to the medical image diagnosis apparatus 1 and the imaging device 3.

The storage circuitry 25 stores therein the preset information, the shape data about the peripheral device and facility, the irradiation route, and the like that are described as being stored in the aforementioned storage circuitry 103.

Then, the ultraviolet-ray irradiation apparatus 2b causes the processing circuitry included in the irradiation control unit 20 to perform an irradiation controlling function 20a. The irradiation controlling function 20a performs the process similar to the aforementioned irradiation controlling function 104b. That is to say, the irradiation controlling function 20a controls the operation of the movable part of the imaging unit 12 by transmitting the control signal or the positional data to the medical image diagnosis apparatus 1. In addition, the irradiation controlling function 20a controls the emission of the ultraviolet ray from the ultraviolet light source 22 by transmitting the control signal to the light source control circuitry 21. In addition, the irradiation controlling function 20a controls the operation of the movable part of the arm mechanism 24 by transmitting the control signal or the positional data to the arm mechanism control circuitry 23.

In addition, the irradiation controlling function 20a acquires the three-dimensional image data or shape data in the examination room by controlling the imaging device 3 and determines the irradiation range or the irradiation route. The irradiation controlling function 20a determines the timing of performing the sterilization process, the irradiation range, the irradiation route, and the like on the basis of the information stored in the storage circuitry 25.

Described with FIG. 15 is the case where the irradiation control unit 20, the light source control circuitry 21, and the arm mechanism control circuitry 23 are included in the configurations and these elements perform the respective processes; however, the embodiment is not limited to this example, and the processes performed by the respective configurations may be performed by one processing circuitry. For example, the processing circuitry included in the irradiation control unit 20 may be configured to collectively perform the processes that are performed by the light source control circuitry 21 and the arm mechanism control circuitry 23. That is to say, the processing circuitry included in the irradiation control unit 20 may perform the controlling function that is described as being performed by the light source control circuitry 21 and the controlling function that is described as being performed by the arm mechanism control circuitry 23.

Here, the processing circuitry included in the irradiation control unit 20 is achieved by a processor, for example. In this case, each processing function described above is stored in the storage circuitry 25 as a computer-executable computer program. The processing circuitry included in the irradiation control unit 20 achieves the function corresponding to each computer program by reading and executing the computer program stored in the storage circuitry 25. In other words, the processing circuitry included in the irradiation control unit 20 having read out the computer program has the processing function illustrated in FIG. 15.

The processing circuitry described in the present specification may be formed by combining a plurality of independent processors, and each processing function may be achieved when each processor executes the computer program. In addition, the respective processing functions of the processing circuits may be achieved dispersedly or integrally in one or a plurality of processing circuits as appropriate. The respective processing functions of the processing circuits may be achieved by a combination of hardware such as a circuit and software. Here, although the computer program corresponding to each processing function is stored in one storage circuitry in this example, the embodiment is not limited to this example. For example, the computer programs corresponding to the respective processing functions may be dispersedly stored in a plurality of storage circuits and the processing circuitry may read out each computer program from each storage circuit and execute the computer program.

In the aforementioned embodiments, the irradiation control unit in the present specification is achieved by the irradiation controlling function of the processing circuitry; however, the embodiments are not limited to this example. For example, the irradiation control unit in the present specification that is achieved by the irradiation controlling function in the embodiments may alternatively be achieved by hardware only, software only, or a combination of hardware and software.

The term "processor" used in the above embodiments mean, for example, a central processing unit (CPU), a graphics processing unit (GPU), an application specific integrated circuit (ASIC), a programmable logic device (for example, simple programmable logic device (SPLD)), a complex programmable logic device (CPLD), a field programmable gate array (FPGA), or the like. Here, instead of saving a computer program in the storage circuit, the computer program may be directly incorporated in a circuit of the processor. In this case, the processor achieves the function by reading and executing the computer program incorporated in the circuit. Each processor in the present embodiment is not limited to the processor configured as one circuit for each processor, and a plurality of independent circuits may be combined into one processor to achieve that function.

Here, the computer program to be executed by the processor is provided by being incorporated in a read only memory (ROM), a storage circuit, or the like in advance. Note that this computer program may be stored in a computer-readable non-transitory storage medium such as a compact disc ROM (CD-ROM), a flexible disk (FD), a CD-recordable (CD-R), or a digital versatile disc (DVD) in a format that can be installed or executed in these devices. This computer program may be stored on a computer connected to the network such as the Internet, and provided or distributed by being downloaded through the network. For example, this computer program is configured by a module including each of the aforementioned processing functions. Regarding the actual hardware, a CPU reads out the computer program from the storage medium such as a ROM and executes the computer program, so that each module is loaded on a main storage device and generated on the main storage device.

In the aforementioned embodiments, the components of the devices in the drawings are conceptual in terms of function, and are not necessarily configured exactly as illustrated in the drawings in the physical point of view. That is to say, the specific mode of the dispersion or integration of the devices is not limited to the mode illustrated in the drawings, and a part of or all of the devices may be dispersed or integrated functionally or physically in an arbitrary unit in accordance with various loads, use circumstances, and the like. In addition, each processing function performed in each device can be achieved in an arbitrary part or entirely by the CPU and the computer program analyzed and executed in the CPU, or can be achieved as the hardware by wired logic.

Among the processes described in the aforementioned embodiments, all of or a part of the processes described as being performed automatically can be performed manually or all of or a part of the processes described as being performed manually can be performed automatically by a known method. In addition, the procedure of the process, the procedure of the control, the specific names, and the information including various data and parameters in the above description or the drawings can be changed arbitrarily unless stated otherwise.

According to at least one of the embodiments described above, stable hygiene management can be achieved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis apparatus, comprising:
   an ultraviolet light source configured to emit an ultraviolet ray;
   processing circuitry configured to control irradiation of the ultraviolet ray to an irradiation object irradiated with the ultraviolet ray in an examination room by moving a position of the ultraviolet light source relatively with respect to the irradiation object; and
   a medical imaging apparatus including a detector and configured to acquire a medical image of a subject,
   wherein the processing circuitry is further configured to
      control, when determining that a subject examined in the examination room before the irradiation of the ultraviolet is not infected with an infectious disease, the irradiation of the ultraviolet ray to an area contacted by the subject in the examination room, and
      control, when determining that the subject examined in the examination room before the irradiation of the ultraviolet is infected with the infectious disease, the irradiation of the ultraviolet ray to an entirety of the examination room.

2. The medical image diagnosis apparatus according to claim 1, wherein the processing circuitry is further configured to control the irradiation of the ultraviolet ray to the irradiation object by changing the position of the ultraviolet light source with respect to the irradiation object.

3. The medical image diagnosis apparatus according to claim 2, wherein the processing circuitry is further configured to control the irradiation of the ultraviolet ray to the irradiation object by moving the irradiation object so as to change the position of the ultraviolet light source relatively with respect to the irradiation object.

4. The medical image diagnosis apparatus according to claim 1, wherein the processing circuitry is further configured to control the irradiation of the ultraviolet ray to the irradiation object by moving the irradiation object so as to change the position of the ultraviolet light source with respect to the irradiation object.

5. The medical image diagnosis apparatus according to claim 1, wherein the processing circuitry is further configured to specify an irradiation range on the irradiation object and control the irradiation with the ultraviolet ray in the specified irradiation range.

6. The medical image diagnosis apparatus according to claim 5, wherein the processing circuitry is further configured to specify the irradiation range on the irradiation object, based on a piece of preset information selected from a plurality of pieces of preset information in which the irradiation range is defined for at least one of an examination process or protocol and an examination part, and control the irradiation with the ultraviolet ray in the specified irradiation range.

7. The medical image diagnosis apparatus according to claim 5, wherein
   the irradiation object includes a device and a facility in the examination room, and
   the processing circuitry is further configured to specify the irradiation range on the device and the facility in the examination room and control the irradiation with the ultraviolet ray in the specified irradiation range.

8. The medical image diagnosis apparatus according to claim 7, wherein the processing circuitry is further configured to specify the irradiation range on the device and the facility in the examination room, based on at least one of the device and the facility in the examination room included in a piece of preset information selected from a plurality of pieces of preset information in which the irradiation range is defined, and control the irradiation with the ultraviolet ray in the specified irradiation range.

9. The medical image diagnosis apparatus according to claim 7, wherein the processing circuitry is further configured to automatically detect at least one of the device and the facility from the examination room, specify the irradiation range on the device and the facility in the examination room based on a detection result, and control the irradiation with the ultraviolet ray in the specified irradiation range.

10. The medical image diagnosis apparatus according to claim 9, wherein the processing circuitry is further configured to automatically detect at least one of the device and the facility from the examination room, based on a photographing result obtained by an optical photographing equipment disposed in the examination room.

11. The medical image diagnosis apparatus according to claim 10, wherein the processing circuitry is further configured to automatically detect at least one of the device and the facility from the examination room, based on the photographing result obtained when the optical photographing equipment photographs the examination room that is illuminated with light emitted from the ultraviolet light source.

12. The medical image diagnosis apparatus according to claim 1, wherein
the irradiation object includes a device and a facility in the examination room, and
the processing circuitry is further configured to control the irradiation of the ultraviolet ray to at least one of the device and the facility in the examination room by moving the position of the ultraviolet light source relatively with respect to at least one of the device and the facility in the examination room.

13. The medical image diagnosis apparatus according to claim 12, wherein the processing circuitry is further configured to automatically detect at least one of the device and the facility from the examination room, and based on a detection result, control the irradiation of the ultraviolet ray to the at least one of the device and the facility in the examination room.

14. The medical image diagnosis apparatus according to claim 13, wherein the processing circuitry is further configured to automatically detect at least one of the device and the facility from the examination room, based on a photographing result obtained by an optical photographing equipment disposed in the examination room.

15. The medical image diagnosis apparatus according to claim 14, wherein the processing circuitry is further configured to automatically detect at least one of the device and the facility from the examination room, based on the photographing result obtained when the optical photographing equipment photographs the examination room that is illuminated with visible light emitted from the ultraviolet light source.

16. The medical image diagnosis apparatus according to claim 1, wherein the ultraviolet light source is provided to the imaging equipment.

17. The medical image diagnosis apparatus according to claim 16, wherein
the imaging equipment includes a C-arm, and
the ultraviolet light source is provided on the C-arm.

18. The medical image diagnosis apparatus according to claim 16, wherein
the imaging equipment includes a computed tomography (CT) gantry, and
the ultraviolet light source is provided on the CT gantry.

19. The medical image diagnosis apparatus according to claim 16, wherein
the imaging equipment includes a magnetic resonance imaging (MRI) gantry, and
the ultraviolet light source is provided on the MRI gantry.

20. The medical image diagnosis apparatus according to claim 1, wherein
the ultraviolet light source is provided on at least one of the imaging equipment and a couch where the subject is placed, and
the processing circuitry is further configured to move the position of the ultraviolet light source by operating at least one of the imaging equipment and the couch where the subject is placed.

21. The medical image diagnosis apparatus according to claim 1, wherein the ultraviolet light source includes a plurality of light generators.

22. The medical image diagnosis apparatus according to claim 1, further comprising an arm configured to be movable on a travel rail, and to hold the ultraviolet light source, the travel rail being used to move the imaging equipment,
wherein the processing circuitry is further configured to change the position of the ultraviolet light source relatively with respect to the irradiation object by moving the arm on the travel rail.

* * * * *